(12) United States Patent
McCullen et al.

(10) Patent No.: US 10,888,407 B2
(45) Date of Patent: Jan. 12, 2021

(54) METHOD FOR FORMING A MULTI-LAYER CONSTRUCT

(71) Applicant: POLY-MED, INC., Anderson, SC (US)

(72) Inventors: Seth Dylan McCullen, Greenville, SC (US); Clayton Joseph Culbreath, Anderson, SC (US); Michael Aaron Vaughn, Anderson, SC (US); Michael Scott Taylor, Anderson, SC (US)

(73) Assignee: POLY-MED, INC., Anderson, SC (US)

( * ) Notice: Subject to any disclaimer, the term of this patent is extended or adjusted under 35 U.S.C. 154(b) by 0 days.

(21) Appl. No.: 16/060,856

(22) PCT Filed: Dec. 10, 2016

(86) PCT No.: PCT/US2016/000125
§ 371 (c)(1),
(2) Date: Jun. 8, 2018

(87) PCT Pub. No.: WO2017/099820
PCT Pub. Date: Jun. 15, 2017

(65) Prior Publication Data
US 2019/0000602 A1    Jan. 3, 2019

Related U.S. Application Data

(60) Provisional application No. 62/266,008, filed on Dec. 11, 2015.

(51) Int. Cl.
*B29C 41/24* (2006.01)
*B29C 41/26* (2006.01)
(Continued)

(52) U.S. Cl.
CPC ............ *A61F 2/0063* (2013.01); *A61L 27/00* (2013.01); *A61L 27/58* (2013.01); *D01D 5/0038* (2013.01);
(Continued)

(58) Field of Classification Search
CPC ......... B29C 41/24; B29C 41/26; B29C 41/32; B29L 2031/753; B29L 2031/7532;
(Continued)

(56) References Cited

U.S. PATENT DOCUMENTS

2008/0109070 A1* 5/2008 Wagner ............... A61L 27/3843
                                                                623/1.41
2009/0020921 A1* 1/2009 Cakmak ............... D01D 5/0084
                                                                264/484
(Continued)

FOREIGN PATENT DOCUMENTS

| CA | 3007935 | 12/2016 |
|---|---|---|
| EP | 16873488.7 | 12/2016 |
| WO | PCT/US2016/000125 | 12/2016 |

OTHER PUBLICATIONS

International Search Report and Written Opinion dated Jun. 27, 2017, for International Application No. PCT/US2016/000125.
U.S. Appl. No. 62/266,008, filed Dec. 11, 2015, McCullen, et al.

*Primary Examiner* — Leo B Tentoni

(57) ABSTRACT

A composite implant device for use in a medical application, comprising a synthetically-derived mesh that mimics particular critical aspects of a biologically-derived mesh. The composite implant device can be used for the reinforcement and reconstruction of tissues within the body and can be comprised of a majority of synthetic components and minority of naturally-derived components which mimic the structure and function of a naturally-derived mesh.

9 Claims, 9 Drawing Sheets

(51) Int. Cl.
  *B29C 41/32* (2006.01)
  *B32B 5/24* (2006.01)
  *A61F 2/00* (2006.01)
  *A61L 27/00* (2006.01)
  *D01D 5/00* (2006.01)
  *A61L 27/58* (2006.01)
  *B29L 31/00* (2006.01)

(52) U.S. Cl.
  CPC ......... *D01D 5/0076* (2013.01); *D01D 5/0084* (2013.01); *A61F 2210/0004* (2013.01); *A61F 2240/001* (2013.01); *A61F 2250/003* (2013.01); *A61F 2250/0039* (2013.01); *B29L 2031/753* (2013.01); *B29L 2031/7532* (2013.01); *B29L 2031/7534* (2013.01); *B32B 2250/03* (2013.01); *D10B 2509/06* (2013.01); *D10B 2509/08* (2013.01)

(58) Field of Classification Search
  CPC ............... B29L 2031/7534; B32B 5/24; B32B 2250/03; D01D 5/003; D01D 5/0038; D01D 5/0076; D01D 5/0084; D10B 2509/06; D10B 2509/08
  USPC ........ 264/10, 172.19, 173.1, 173.11, 173.12, 264/464, 465, 466, 484
  See application file for complete search history.

(56) References Cited

U.S. PATENT DOCUMENTS

| | | | |
|---|---|---|---|
| 2011/0250689 A1* | 10/2011 | Baaijens | D01D 5/0076 264/465 X |
| 2013/0268062 A1* | 10/2013 | Puckett | D01D 5/003 623/1.44 |
| 2013/0338791 A1 | 12/2013 | McCullen et al. | |
| 2015/0037557 A1 | 2/2015 | Wang et al. | |
| 2015/0182885 A1 | 7/2015 | Thomson et al. | |
| 2015/0239197 A1 | 8/2015 | Hosomi et al. | |
| 2016/0038646 A1* | 2/2016 | Bowlin | A61L 27/24 264/465 X |

* cited by examiner

METHOD FOR FORMING A MULTI-LAYER CONSTRUCT

CROSS-REFERENCE TO RELATED APPLICATION

This application is a national phase application under 35 U.S.C. § 371 of International Application No. PCT/US2016/000125, filed Dec. 10, 2016, which claims the benefit under 35 U.S.C. § 119(e) of U.S. Provisional Patent Application No. 62/266,008 filed Dec. 11, 2015, where these applications are incorporated herein by reference in their entirety for all purposes.

FIELD OF THE INVENTION

The present invention relates to a composite implant device for use in a medical application, comprising a synthetically-derived mesh that mimics certain aspects of a biologically-derived mesh such as composition, mechanical properties, topography, microstructure, and tissue response. The present invention also relates to methods for producing such devices.

BACKGROUND

Despite the expanding sophistication of medical devices, repair and replacement of tissues remains a formidable challenge. In reinforcing applications, implant devices are used for internal support and augmentation of injured and/or diseased tissues. For reconstruction of soft tissue, these implant devices typically comprise a mesh component or mesh-like structures that are able to conform to the native tissue, thereby providing mechanical support, integration into surrounding tissues, and promotion of healing.

Implant meshes are commonly referred to as surgical meshes and include two (2) main classes of material: 1) synthetically-derived meshes made from non-degradable or degradable materials which can provide engineered strength, resorption, and structure, and 2) biologically-derived meshes which are of xenogenic or allogenic origin and have had their cellular content removed providing an extracellular matrix framework. Both of these types of meshes have their benefits and drawbacks which results in a range of usage and choice by the clinician along with a myriad of results as described in the literature.

Synthetically-derived meshes have the advantage of customization that allows for engineering to achieve particular structures and properties as needed for a particular application. This includes engineered strength, engineered porosity, eliminates risks of pathogen transfer, and engineered structure, as well as of the added benefit of being easily molded into different shapes and sizes using various processing techniques. However, certain disadvantages exist for meshes comprised of synthetic materials. These disadvantages, or drawbacks, include a lack of extracellular matrix molecules resulting in a lack of biological activity and minimal ability to elicit beneficial biological responses; the generation of degradation by-products such as lactic and glycolic acid which can have negative effects on the surrounding wound environment and the potential for foreign body reaction that may develop after implantation.

Biologically-derived mesh materials are currently being used to restore tissue defects within the body. The benefits of using biologically-derived mesh materials include their ability to mimic the natural extracellular matrix structure and composition, emulate native stimulatory effects of extracellular matrix on cells, and allow the direct incorporation of growth factors and/or matrix proteins to further enhance cell and tissue function. Drawbacks to using biologically-derived mesh materials include varied degradation kinetics, variability in material consistency based on anatomical location and donor species, and the possible transfer of pathogens.

One mesh in particular that is a leading choice for biologically-derived mesh materials is acellular dermal matrix (ADM) which was first introduced in 1994. ADM is derived specifically from the dermis layer within skin that is located between the epidermis and the subcutaneous tissue. The dermis is approximately 1-4 mm in thickness and divided into two layers, the papillary region and the reticular region. The papillary region is located in the superficial layer that is adjacent to the epidermis, and a deep thicker area known as the reticular region is found deeper within the tissue residing above the hypodermis.

Compositionally, ADM varies zonally which contributes to its function, morphology, and properties. For example, Type IV collagen is restricted to the basal laminae found at the dermal-epidermal junction residing in the papillary region. In regards to composition, Type I and Type III collagens account for the majority of collagens present within the dermis with approximately 80-85% being Type I collagen. In the dermis, Type I collagen appears as large-diameter fibrils that organize into large bundles in the reticular dermis. Type III collagen makes up only 10-15% of the dermal collagen and it forms small-diameter fibrils that are assembled into small-sized fiber bundles. Type I procollagen is found in the upper papillary dermis. Elastic fibers are composed mainly of elastin and are found in the deep reticular dermis.

The papillary dermis consists of two regions: a sub-epidermal band and the papillary dermis proper. The papillary dermis proper contains fine-diameter collagen fibrils that are organized into loosely intermeshed (woven) bundles that are typically smaller than those of the reticular dermis. The fine-diameter fibrils and the small size of the fiber bundles are presumed to be a result of the higher ratio of Type III:I collagen in this region. Compared with the reticular dermis, the papillary dermis has a higher density of cells, a greater proportion of vascular tissue, and compositionally is comprised of different glycosaminoglycans. The sub-epidermal band is a narrow zone of papillary dermis found immediately beneath the basal lamina. This band consists of a diffuse network of fine collagen fibrils that interlace with anchoring fibrils from the basal lamina and elastin fibers. The papillary dermis proper is the structurally stable region of the skin.

The reticular dermis is coarse, densely interwoven bundles of collagen and is characterized by two regions, the uppermost and deep region. The uppermost reticular dermis is comprised of elastin and intermediate sized collagen fibers. The deep reticular dermis contains the largest-diameter fibrils and largest fiber bundles of any dermal region. Within the deep reticular dermis, the composition is mixed between both collagen and elastic fibers.

The papillary and reticular regions have significantly different mechanical properties which may be mostly attributed to the differences in structure at the cellular and molecular levels. For example, the papillary region is tightly connected to the epidermis through a basement membrane and comprised of loosely organized areolar connective tissue below the basement membrane. In contrast, the reticular region forms a thicker composition and is composed of dense and irregular connective tissue and comprised of collagenous, elastic, and reticular fibers that form an intermeshed network. The reticular region of the dermis is responsible for the majority of the strength, extensibility, and elasticity of the tissue while the papillary region forms a membrane-like structure.

As discussed above various structural components form the dermis and include collagen, elastic fibers, and extracellular matrix molecules including anionic polysaccharides such as chondroitin sulfate, dermatan sulfate, and hyaluronic acid. Based on the induced negative charge of the polysaccharide component, ADM possesses the ability to undergo hydration and swelling due to the polarity of water.

Current ADM products are derived from allogenic (human) or xenogenic (porcine, bovine, equine, ovine) sources that has been removed of cellular components (DNA and surface antigens) that would normally cause inflammation and rejection upon implantation. The resulting material is a tissue matrix that promotes intrinsic regeneration properties via autologous cell repopulation, angiogenesis, and normal tissue in-growth, promoting better integration with excellent post-operative healing. ADM has been shown to be useful for reconstruction in a multitude of surgical applications, and ADM comes in a variety of sizes, shapes, and thickness ranging from 0.3 mm to upwards of 2 mm. Typical sizes can range from 4 cm×16 cm, and sizing is dependent on the size of the tissue defect. The overall biological mechanism for the benefit of ADM does vary based on brand and surgical techniques employed. However, ADM products generally strive to preserve the complex composition and three-dimensional ultrastructure of the native extracellular matrix. During processing of tissues to create ADM, it is accepted and understood that some degree of disruption will occur to the composition and to a lesser extent the architecture of the native tissue, and therefore variation is expected from piece to piece.

ADM has been implemented for multiple indications including dental surgery, burn reconstruction, eyelid reconstruction, hand surgery, lower extremity coverage, nasal reconstruction, pelvic floor reconstruction, as well as scalp reconstruction. The use of ADM has been highly regarded for abdominal wall reconstruction and breast reconstruction and was first used for these types of procedures in 2001. Since then, the use of ADM has expanded in the reconstruction space; however, there have been a wide range of positive and negative results depending on the type of ADM used, the particular surgical technique, and patient population. In general, ADM products strive to preserve the complex composition and three-dimensional ultrastructure of the native extracellular matrix. During processing of these tissues, it is accepted that some degree of disruption will occur to the composition and to a lesser extent the architecture of the native tissue.

ADM may be provided in dry or hydrated forms, although typical procedures require ADM to be hydrated within a short time frame that can range anywhere from three (3) to thirty (30) minutes prior to placement. Further, the surgical performance of ADM is also dependent on the appropriate determination of ADM surface polarity and the subsequent implantation according to that determination. The two ADM surfaces are very different in structure and topography and can serve different functions, so it is critical to identify the two sides correctly when used in a surgical procedure. The first side of ADM is the recticular region, and this surface is known to readily absorb blood when placed in contact with the wound bed. This is due to its ability to allow for revascularization which is afforded by its large surface area and fibrillar nature. The opposing side of ADM is the papillary region and features a dull, roughened appearance due to the basement membrane. It should also be noted that the inherent tackiness of the ADM surfaces assists with adherence to other biological tissues.

A recent study examined the physical and biochemical properties of two (2) well known products: AlloDerm® and AlloMax™. Evaluation of these two matrices showed Alloderm® contains significantly higher amounts of growth factors bFGF, VEGF, and TGF-β1 which are known to stimulate wound healing and tissue growth. However, in addition to possessing enhanced levels of these growth factors, AlloDerm® contained approximately 1,500 nanograms (ng) of double-stranded DNA (dsDNA) per milligram (mg) of dry weight. This is in comparison AlloMax™, which was found to have less than 0.25 ng dsDNA per mg of dry weight. This study showed significant differences in not only the physical features of these two ADM's but also in the amounts of residual biological content (i.e. ng dsDNA/mg dry weight) which could explain the variable results and significant differences in the respective clinical studies for these products.

In addition to the heterogeneity experienced between ADM brands based on biological source and processing technique, another factor that is prohibitive and discourages the use of ADM is its high cost, which can be as high as US$5,000 per piece. Overall, this material seems to display extremely desirable properties from a handling and "surgical feel" perspective based on its handling, wettability, and ability to stretch.

Prior attempts at bioabsorbable barrier composites exist in the prior art. For instance, US 2010/0074941, Shalaby discloses a composite formed of a flexible film and at least one fibrous or microfibrous adjoining component in the form of knitted mesh or electrospun, non-woven fabric. These composites can be tailored/customized to allow their use in neurological and urinogenital surgical procedures and particularly those associated with spine, cranial and urinary bladder prostheses. Due to their flexibility and barrier properties, these composites are suitable for use in the prevention of adhesion formation following several types of surgical procedures. However, the intended purpose and function of the constructs disclosed in the reference are directed to absorbable barrier composites with modulated gas and water permeability. The embodiments disclosed in the reference are not specifically engineered to mimic the structure or properties of ADM in a synthetic format, even though they may be intended for use in a multitude of surgical procedures. Prior attempts do not disclose how to mimic the structure or properties of ADM in a synthetic format. The reference, however, fails to specifically teach or suggest how to fabricate the constructs disclosed herein, and the reference also fails to provide a teaching or motivation for making such constructs.

In U.S. Pat. No. 5,795,584, Totakura discloses a surgical adhesion barrier having at least one layer of a bioabsorbable material comprising copolymers and/or block copolymers derived from trimethylene carbonate. The barrier can be comprised of multilayers which reduce the occurrence of post-surgical adhesions. This barrier is intended to not allow cellular attachment, adhesion, or ingrowth, and moreover not to replicate the natural tissue structure. Totakura does not disclose the barrier as a means to replicate the topography or structure of natural tissue as found in ADM based products, which are designed to support and promote the adhesion and ingrowth of autologous cells and tissues.

U.S. Pat. No. 6,319,264 to Tormala, et al. discloses a degradable, multi-layered mesh implant designed specifically for closing hernia defects. While the reference describes the invention as having at least two functional components or layers, the layers are engineered for very specific purposes that are not consistent with a construct of the current disclosure. In particular, the implant is comprised of a fibrous layer that requires a rapidly degradable layer, a second layer which is more slowly degradable layer, and optionally a third layer in the form of a degradable film. The reference does not disclose, nor does it teach, the importance of certain methods suitable for adjoining the multiple layers together to reduce or prevent delamination. Further, the reference does not teach or suggest the use of elastomeric degradable materials that are critical for making a synthetic construct that mimics certain properties of biologically-derived meshes. Moreover, the present invention and its various embodiments do not require certain degradation rates for specific layers. The degradation rate of the multiple layers of the composite implant device is not necessarily relevant and not limiting. Furthermore Tormala requires the preferential placement of the hernia mesh within the body in order to support the repaired hernia defect during healing and reduce or prevent adhesion complications.

Additionally, US 2015/0151024, Shalaby, discloses fibrous composite constructs that include reinforcement of composite fibrous meshes. These constructs include two groups of bioabsorbable matrices of segmented polyaxial copolyesters reinforced with yarn constructs including a biostable yarn and at least one bioabsorbable yarn. However, the reference does not disclose how to mimic the structure and properties of ADM in a synthetic format nor are the composites fully bioresorbable. Further, it does not include the use of biomolecules as an additive and minor component within the construct, nor does it disclose the creation of a directional or zonally organized hydrating gradient.

Accordingly, it is an object of the present invention, in light of the disadvantages of current surgical mesh devices, to provide a surgical mesh with the beneficial attributes of ADM along with the benefits of a synthetically-derived surgical mesh. This need includes a mesh material which is biocompatible, resorbable, offers tailored, engineered mechanical properties, afforded by the synthetic mesh, and desirable handling properties, afforded by designing to mimic a biologically-derived mesh.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The above objectives are accomplished according to the present invention by providing a synthetic, composite, laminate implantable medical device. In one embodiment, that implantable medical device mimics the structure, organization, and properties of biologically-derived mesh materials, which include ADM and related constructs. The invention may include the combination of synthetic and naturally-derived materials to mimic the properties of biologically-derived mesh materials for use in tissue augmentation, repair, and replacement.

In one embodiment, the present disclosure provides a synthetic mesh comprising a bioabsorbable copolyester; and at least two layers. The mesh may be entirely synthetic, or it may include synthetic components, where a synthetic material is not found naturally in nature. In one embodiment, these at least two layers both comprise fibrous material, however are distinct from one another in terms of the average diameter of the fibers contained in each layer. In one embodiment, one of the at least two layers (the first fibrous layer) directly adjoins a base layer, and another of the at least two layers (the second fibrous layer) directly adjoins the first fibrous layer but does not directly adjoin the base layer, where the first fibrous layer has a preponderance of smaller diameter fibers than the second fibrous layer. For example, the at least two layers may be a first fibrous layer and a second fibrous layer, where the first layer has fibers with an average fiber diameter in the range of 2-10 µm and the second layer has fibers with an average fiber diameter in the range of 0.5-5 µm. Optionally, the mesh may be further characterized by specifying that the first layer contains few or no fibers having diameter in the range of 0.5-5 µm, where few refers to less than 25%, or less than 20%, or less than 15%, or less than 10%, or less than 5%, or less than 1% of the fibers present in the first layer. Similarly, the mesh may be further characterized by specifying that the second layer contains few or no fibers having diameter in the range of 2-10 µm, where few refers to less than 25%, or less than 20%, or less than 15%, or less than 10%, or less than 5%, or less than 1% of the fibers present in the second. Optionally, the mesh is entirely synthetic, although in one embodiment less than 10% by weight of the mesh is non-synthetic.

In another embodiment, the present disclosure provides a composite implant device for soft-tissue fixation, repair, augmentation, or replacement comprising a laminate from multiple phases. The laminate is able to include multiple morphologies, structures, and properties and does not undergo delamination of the individual laminates or components during tensile loading or when subjected to a deforming load.

In another embodiment, the present disclosure provides an implantable composite synthetic laminate for soft tissue fixation, repair, augmentation, or replacement with a gradient in tensile elasticity in the z-direction wherein the base layer is comprised of a more solid layer, which may optionally be porous, yet displays enhanced compliance (stretchiness) properties compared to other layers of the laminate. The other laminate layers of the implant display decreased compliance compared to the base layer. The implantable device comprises a laminate structure wherein the base layer is comprised of a film, a fiber-reinforced layer that directly adjoins the base layer, and a superior fibrous layer that directly adjoins the fiber-reinforced layer.

In another embodiment, the present disclosure provides an implant that matches one or more of certain mechanical properties of natural tissues. Tissues can display isotropic, anisotropic, or orthotropic properties based on the structure and composition of tissue in question. Orientation of the implant relative to the surrounding and underlying tissue may be important since the direction for loading for tissue corresponds to their function. The implants of the present disclosure may be used for one or more of muscular, musculoskeletal, connective, and membrane tissue replacement.

In another embodiment, the present disclosure provides for the prevention of tissue adhesion with underlying organs or other tissue structures. In one optional embodiment, the present disclosure provides an anti-adhesion component in the implant to limit unwanted tissue attachment to extraneous surrounding organs and tissues. Tissue adhesion may also be prevented by one or more of minimizing surface area, surface roughness, three-dimensionality, while increasing hydrophilicity to minimize cellular/tissue attachment and ingrowth.

In another embodiment, the present disclosure provides for the ability to allow tissue ingrowth into a device by the presence of macroscopic or microscopic features which can promote cellular infiltration, proliferation, and differentiation. For example, the base layer of the construct may be porous to allow tissue ingrowth.

In another embodiment, the present disclosure provides a multilayer construct having the ability to resist delamination of the laminate layers under high tensile strains or repeated cyclical loading. Composites of varying morphologies and properties have a propensity to undergo delamination at strains above the breaking strength or load of the weakest component.

In another embodiment, the present disclosure provides the ability to vary mechanical properties in a planar fashion by introduction of network or pores, cuts, apertures, slits, as well as material thickness. The disclosure further provides gradient in thickness to generate a construct suitable to replace tissues of different physical properties.

Further embodiments of the present disclosure are directed to very specific mechanical and physical properties, structure and features that are necessary to mimic naturally-derived ADM.

In further embodiments, the present disclosure provides a multi-layered material/construct having the ability to form a gradient that hydrates away from the base layer. In other words, one or more layers other than the base layer generally have greater hydrating ability than does the base layer, so that moisture is taken away from the base layer. Optionally, the layer furthest from the base layer has the greatest hydrating ability, and intermediate layers have intermediate hydrating ability.

In a further embodiment, the present disclosure provides multiple layered materials with various properties such as described hereinafter. For example, in a further embodiment the present disclosure provides a multiplayer construct that has, or closely mimics, the properties of ADM. For example, in a further embodiment the present disclosure provides a composite implant device comprising fibrous layers which mimic the size scale of the natural extracellular matrix present within ADM as well as topographical features.

In another embodiment, the present disclosure provides a method of forming a synthetic mesh. The method comprises dissolving an elastomeric, bioabsorbable copolyester polymer in a solvent; forming a homogenous solution which may optionally be tinted; evaporating the solvent to form a film; and coating the film with at least two layer forming solutions to form a multilayered mesh.

In another embodiment, the present disclosure provides a method of forming a synthetic mesh. The method comprises extruding an elastomeric, bioabsorbable copolyester polymer into a planar construct, and coating the film with at least two layer forming solutions to form a multilayered mesh.

The above-mentioned and additional features of the present invention and the manner of obtaining them will become apparent, and the invention will be best understood by reference to the following more detailed description. All references disclosed herein are hereby incorporated by reference in their entirety as if each was incorporated individually This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments; Other features, objects and advantages will be apparent from the description, the drawings, and the claims.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein Examples of the invention are shown and wherein.

Figure 1:
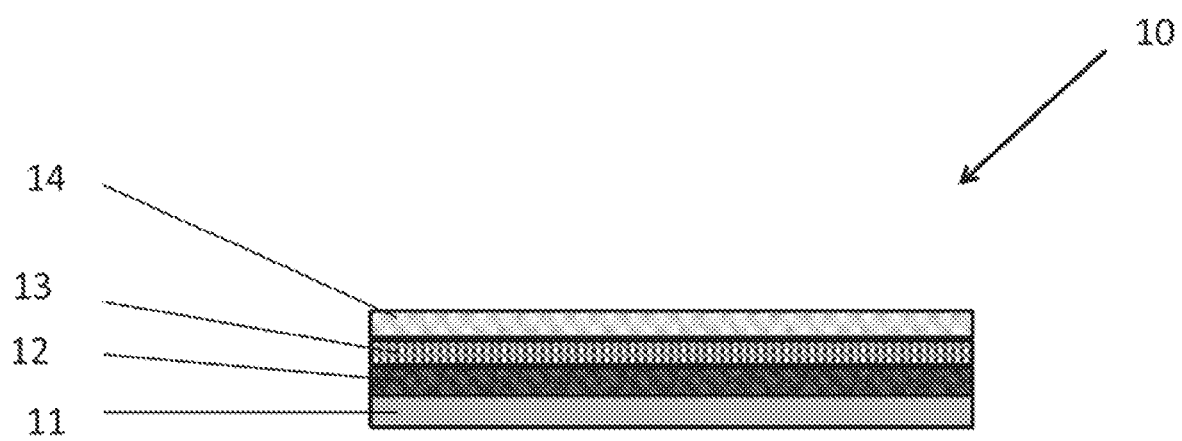
FIG. 1 shows a cross-section of the implant device 10 which is comprised of multiple layers. The implant device 10 is comprised of multiple layers including a base layer 11, a first layer 12, a second layer 13, and a third layer 14.
Figure 2:
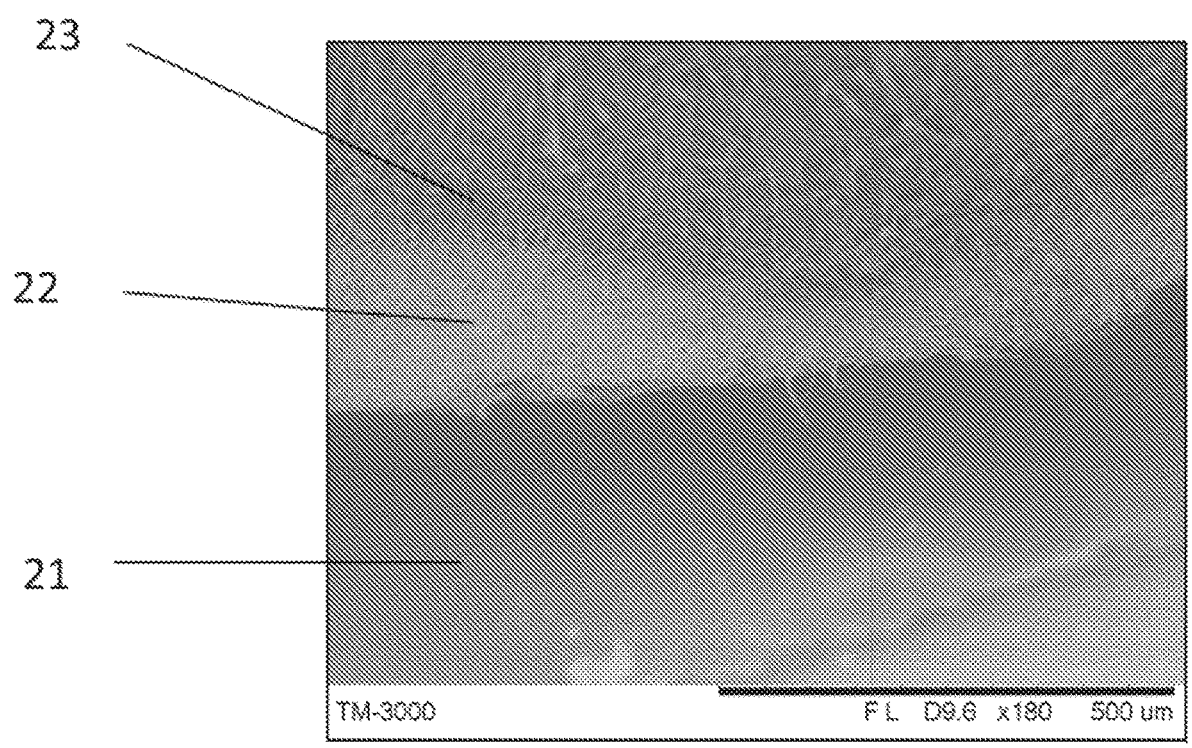
FIG. 2 shows an SEM image of the prototype from FIG. 1, in cross-section depicting the multiple layers, specifically, base layer 21, fibrous component 22, and fibrous surface 23 of the implant device.
Figure 3:
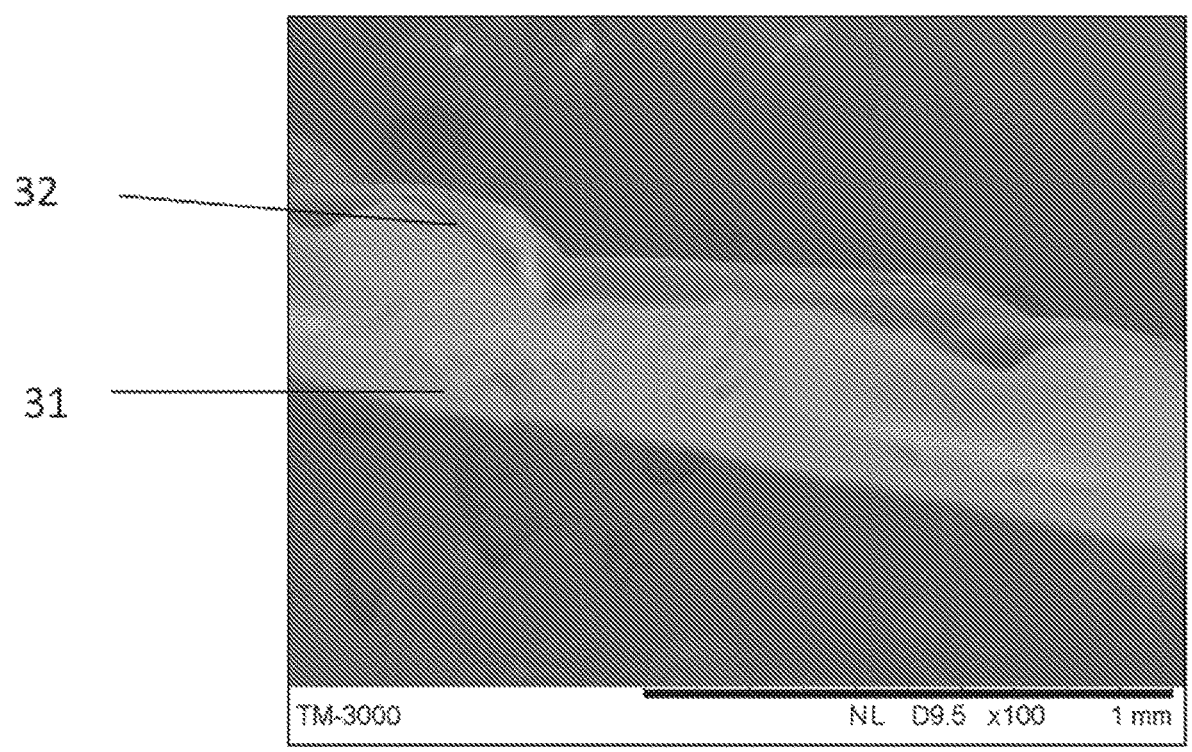
FIG. 3 shows an SEM image of a second prototype in cross-section with the underlying base layer 31 and fibrous component 32.
Figure 4:
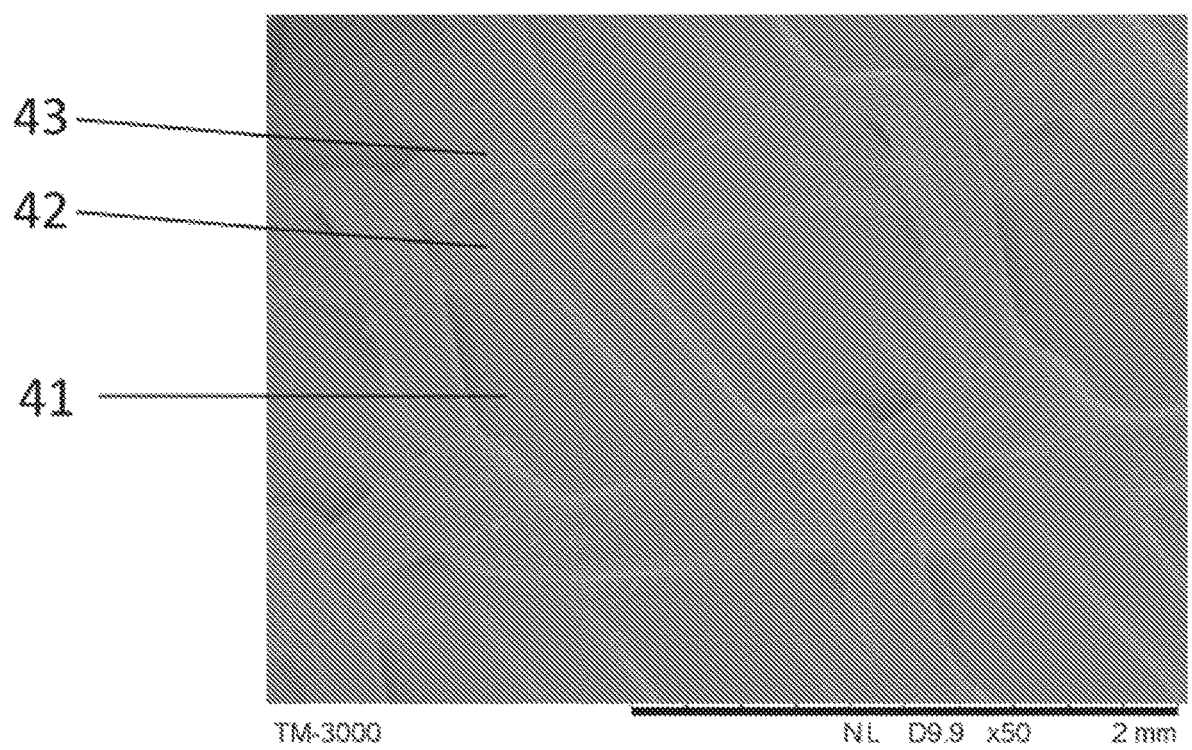
FIG. 4 shows an SEM image of the second prototype in top-down view demonstrating the underlying base layer, the fibrous component reinforcing the base layer 42, and the fibrous component superior to an underlying base layer 43.

It will be understood by those skilled in the art that one or more aspects and embodiments of this invention can meet certain objectives, while one or more other aspects or embodiments can meet certain other objectives. Each objective may not apply equally, in all its respects, to every aspect of this invention. As such, the embodiments disclosed herein can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF THE INVENTION

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

In one embodiment, the constructs of the present disclosure include fibrous material. As used herein, a fiber refers to a thread or filament having an aspect ratio of at least 100:1. A fibrous layer, and a fibrous material, will each include a plurality of fibers. In one embodiment, the constructs of the present disclosure are meshes. As used herein, a mesh refers to a construct that includes, as at least one component, a porous material made of a network of fibers. The mesh may optionally be described as a 2-dimensional mesh, where the thickness of the mesh is small, e.g., less than 10% of, or less than 5% of, or less than 1% of the larger of the length and width of the mesh. The construct of the present disclosure may be referred to as a laminate, which means that the composite includes two or more distinct layers that contribute to the thickness of the composite, where those layers are distinct in that they are different from one another.

In one embodiment, the present disclosure provides a composite, laminate implantable medical device, comprising: (i) a base layer comprising an elastomeric, copolyester polymer film, the base layer having a top side, a bottom side, and a thickness; (ii) a first layer comprising a first plurality of fibrous elements comprising at least one fiber population which displays elastomeric properties and is reinforced and adjoined to at least a portion of the top side of the base layer thereby obtaining a laminate implantable device; (iii) a second layer comprising a second plurality of fibrous elements comprising at least two fiber populations adjoined and affixed to the first layer, and (iv) a third layer comprising a plurality of particulate and/or fibrous elements comprised of at least one particulate/fiber population adjoined to the second layer.

Both the base layer and the first layer may display elastomeric properties wherein each layer can undergo deformation and return to its original dimensions upon removal of a deforming force. The base layer and first layer may be integrated such that the first layer may reinforce the base layer where the two layers are connected in a manner to not undergo delamination wherein the first layer is physically affixed to the base layer. Both the base layer and first layer may be able to undergo deformation when a deforming load is applied, where in various embodiments the strain at break for both layers is greater than 100% strain at break, or greater than 200% strain at break, or greater than 300% strain at break, or greater than 400% strain at break, or greater than 500% strain at break.

The base layer may be able to mimic and replicate the physical properties of the papillary region of ADM and may be considered to be similar in function to a basement membrane. The first layer may be fully integrated into the base layer and cross-sectional analysis of these two layers may display an interconnected region. The first and second layers may comprise multiple pluralities of fibers which are further defined by fiber size, areal density, pore size, mechanics, orientation, thickness, material composition, among others. The third layer may comprise particles of multiple geometries and/or fibrous elements and can include the use of bioabsorbable copolyesters with enhanced hydrating properties (i.e. wettability) as well as lubricity properties compared to the second and first layer.

In some embodiments the third layer may comprise the use of biomolecules in conjunction or separately with bioabsorbable copolyesters. The first, second, and third layers mimic and replicate the function of the reticular region of ADM, offering a fibrous region with enhanced swelling properties, hydration properties, cellular attachment, and cellular ingress properties compared to the base layer.

The base layer may have a thickness, as measured according to ASTM D1777, Of greater than 25 microns, preferably greater than 50 microns, preferably greater than 75 microns, and more preferably greater than 100 microns. The base, layer may have a thickness within the range of 50-300 microns, preferably in the range of 75-300 microns, and more preferably greater than 50 microns but less than 500 microns, or greater than 100 microns but less than 400 microns, or greater than 100 microns but less than 500 microns.

The base layer may have a porosity of less than 50%, or less than 40%, or less than 30%, or less than 20%. The base layer may have a porosity within the range of 20-0%. Percent porosity may be measured visually, e.g., with a microscope and using, e.g., ImageJ software available from National Institutes of Health, USA. The base layer may exhibit a pore diameter of less than 0.3 mm, or less than 0.2 mm, or less than 0.1 mm. In one embodiment, the base layer is adjoined directly to the first layer. The base layer may have a roughened surface by the inclusion of porogenic materials which can include poly(ethers), poly(ether esters), sulfopolyesters, salts, sugars, inorganic bases such as sodium or potassium phosphate, biomolecules such as gelatin, collagens, peptides, oligosaccharides, and polysaccharides such as hyaluronic acid and its derivatives, chondroitin sulfate and dermatan sulfate. These can be included by direct addition and intermixing with the major synthetic component of the base layer. The addition of such components can provide desired properties such as hydration, delivery of desired biomolecules, material recognition for cells, and tissue adherence.

The base layer may exhibit an areal density of 10-1000 g/m$^2$, or from 10-750 g/m$^2$, and preferably an areal density of 10-500 g/m$^2$. The base layer may exhibit a strain at break greater than 100% and less than 2500%. The base layer may be colored by inclusion of a dye for ease of identification by the clinician when in use. This is accomplished by incorporation of a biocompatible dye within the production of the base layer. The biocompatible dye content can is preferably less than 400 ppm, preferably less than 200 ppm and more preferably less than 100 ppm. The biocompatible dye content is preferably in the range of 20-80 ppm.

In some embodiments the first layer may be described as fibrous. The first layer may be adjoined directly to the base layer and may be comprised of a plurality of fibrous elements. Suitable ranges for fiber diameter include from 0.0001-1 mm, from 0.001-0.1 mm, from 0.01-1 mm, and most preferably a fiber diameter of from 0.001-0.1 mm. Electrospun fibers are preferably used to form the first layer, and such fibers may have diameters ranging from 0.001 mm to 0.030 mm. Melt-extruded fibers are also suitable for forming the first layer; and the diameters are larger and may range from 0.010-1.000 mm, or from 0.040-1.000 mm; however, preferable diameters are within the range of 0.040-0.400 mm, preferably 0.050-0.300 mm, and more preferably 0.100-0.200 mm. In a further embodiment, the first layer may be comprised of an elastomeric bioresorbable copolyester material with mechanical properties that mimic the base layer.

In an alternative, embodiments of the first layer may be described as a film or substantially non-porous sheet, wherein the layer is formed from a polymer, a combination of polymers, or a polymer in combination with a non-polymeric additive. In some embodiments the fibrous layer may comprise one or more elastomeric fibers formed from a biocompatible polymer. In one embodiment the fibrous layer comprises one type of elastomeric fiber formed from a biocompatible polymer. For embodiments incorporating an elastomeric fiber, the biocompatible polymer is preferably a bioabsorbable polyester. Bioabsorbable polyesters may include copolymers formed from L-lactide, DL-lactide, glycolide, ε-caprolactone, para-dioxanone, 1,5-dioxepane-dione, a morpholinedione, trimethylene carbonate or combinations thereof. In some embodiments the copolymer is a block copolymer, a segmented copolymer, or a segmented block copolymer. For the purposes of this disclosure, the segmented block copolymer refers to a block copolymer containing polymeric segments found in at least one block of the copolymer.

In one embodiment, the first layer is comprised of an elastomeric, bioabsorbable copolyester which exhibits mechanical properties that mimic the base layer. The first layer may be constructed entirely from a knitted mesh, or electrospun fibers, or a combination of a knitted mesh and electrospun fibers. For embodiments where a knitted mesh and electrospun fibers are utilized in combination, the electrospun fibers may form a surface coating on one side of the knitted mesh, or the electrospun fibers may encapsulate the knitted mesh and be found on both surfaces of the mesh. Along the edges of such constructs, electrospun fibers may or may not be present. In some embodiments, electrospun fibers may be deposited onto the surface of a knitted mesh to form a thin coating. Further, additional fibrous components are suitable for use in forming the first layer. These include islands in the sea fibers, microfilaments, melt-blown constructs, air-laid constructs, physically entangled constructs formed from either staple fiber or continuous yarn, or any combination thereof. In one embodiment, each of the first and second fibrous layers comprise electrospun fibers.

When present, the thin electrospun coating has a minor contribution to the overall thickness of the layer. The electrospun coating preferably contributes less than 50% to the total thickness of the knitted mesh-electrospun coating layer. In some embodiments, the electrospun coating interfaces directly with a second layer.

Suitable methods that may be used for adjoining the surface of one layer of a construct to the surface of a second layer of a construct include, but are not limited to, the use of adhesives, heating means, solvent welding, ultrasonic welding, sewing, physical entanglement, or any other suitable means for adjoining the surfaces of different layers. Methods involving heating means may optionally involve melting one or more layers to accomplish adjoinment of one surface to another.

In some embodiments, the two or more layers are adjoined by a single method or a combination of two or more methods. In one embodiment, a single method for adjoining layers is utilized to adjoin all layers of the construct. In another embodiment, two different methods suitable for adjoining layers are used in forming the multi-layer construct. One method suitable for adjoining layers may be used for adjoining two layers, and a second and different second method may be used for adjoining one of the two layers adjoined by the first method to a third layer. Alternatively, the two different methods suitable for adjoining layers may be used in combination to adjoin the surfaces of two layers. Further, the two different methods suitable for adjoining layers may be used in combination to adjoin the surfaces of three layers. Optionally, multiple combinations of surface-adjoining methods may be utilized to form a multi-layer construct comprising three, four, five or more distinct layers. Multiple combinations of surface-adjoining methods can be beneficial in forming constructs comprising three, four, five or more distinct layers particularly for constructs that contain different polymeric materials, or for constructs that contain layers formed from the same polymeric materials but found at different ratios. Such "different combinations of polymeric materials" may be used to refer to different chemical compositions for polymeric components, different ratios of polymeric materials, or a combination of different chemical compositions for polymeric components and different ratios of polymeric materials. Ratios of polymeric materials may be described in terms of weight ratios or molar ratios.

In one embodiment, the two layers are adjoined by direct addition of the first layer to the base layer by an electrospinning technique utilizing a high mass addition rate, followed by deposition of the second layer onto the surface of the first layer by electrospinning at a lower mass addition rate. By producing the first layer at a higher mass deposition rate than the rate used for producing the second layer, the first layer can be comprised of a plurality of fibers from a highly solvated polymer system that directly adheres the dissolved polymer to the base layer surface prior to complete evaporation of solvent.

In another embodiment, the first layer can be produced and adhered to the base layer by using a higher concentration of polymer compared to the concentration of polymer used to form the second layer. Both layers may be created at comparable mass deposition rates, and the differences in concentration of polymer may be used to create a higher fiber population density for the first layer relative to the second layer.

In some embodiments, the second layer may be comprised of at least two independent fiber populations which exhibit varying mechanical properties in regards to tensile strain at break with the major fiber population exhibiting a tensile strain at break less than 100% and the minor fiber population exhibiting a tensile strain at break greater than 100% with respect to each other. Incorporation of these two different fiber populations allows the second layer to be conforming (i.e. flexible without tearing) afforded by the minor fiber population, sufficient tensile strength afforded by the major fiber population, and mimics the varying composition of the papillary region of ADM. The major fiber population in some instances represent collagen fibers present within ADM with the minor fiber population representing other ADM constituents.

The minor fiber population of the second layer may be comprised of an elastomeric, biocompatible, bioabsorbable polymer and the major fiber population may be comprised of a second bioabsorbable polymer which is not elastomeric in nature. As used herein, an elastomeric material refers to a material that is able to regain its original shape when a load is removed from the material. A polymer that is not elastomeric in nature will either break when a sufficient load is applied, or will stretch upon application of a sufficient load but Will not return to its original shape when that load is removed. Both fiber populations of the second layer can be comprised of bioabsorbable polymers derived from at least one cyclic monomer selected from the group consisting of glycolide, L-lactide, DL-lactide, ε-caprolactone, trimethylene carbonate, para-dioxanone and combinations thereof. Such polymers are preferably polyesters that are formed by ring-opening polymerization conducted at elevated temperature (greater than 100° C., except for para-dioxanone based polymers that may be polymerized between 85° C. to 120° C.) in the presence of an initiator bearing hydroxyl groups and catalyst. Other suitable bioabsorbable polymers include but are not limited to, polyether-ester block copolymers, polyether-ester-urethanes (derived preferably from aliphatic diisocyanates), polyester-carbonate-urethanes and polyester-urethanes. The different polyurethanes as disclosed here include polyurethane-ureas and variations thereof. Such variations may contain a plurality of ester, ether, or carbonate groups and combinations thereof as segments or blocks, in addition to urethane and urea groups. The bioabsorbable polymers suitable for use in constructing the second layer may be of different structures which include, but are not limited to, linear, star, branched and graft configurations.

In one embodiment, at least two of the at least two layers of a construct or mesh of the present disclosure comprise fibrous material, however the layers are distinct from one another in terms of the average diameter of the fibers contained in each layer. In one embodiment, one of the at least two layers (the first fibrous layer) directly adjoins a base layer, and another of the at least two layers (the second fibrous layer) directly adjoins the first fibrous layer but does not directly adjoin the base layer. In one embodiment, the fibers of the first fibrous layer are, on average, of larger diameter than the fibers of the second fibrous layers. Alternatively, in one embodiment, the fibers of the first fibrous layer are, on average, of smaller diameter than the fibers of the second fibrous layers.

For example, the mesh or construct or laminate (these terms being used interchangeably herein) may be prepared such that the fibers closest to the base layer have, on average, the largest fiber diameter, and the average fiber diameter of the fibers decreases with increasing distance from the base layer. Thus, for instance, the first fibrous layer may have a preponderance of larger diameter fibers compared to the diameter size of the fibers contained in the second fibrous layer. For example, the at least two layers may be a first fibrous layer and a second fibrous layer, where the first layer has fibers with an average fiber diameter in the range of 2-10 μm and the second layer has fibers with an average fiber diameter in the range of 0.5-5 μm. Other suitable diameter sizes are provide elsewhere herein.

Optionally, the mesh or construct may be further characterized by specifying that the first layer contains few or no fibers having diameter in the range of 0.5-5 μm, where few refers to less than 25%, or less than 20%, or less than 15%, or less than 10%, or less than 5%, or less than 1% of the fibers present in the first layer. Similarly, the mesh may be further characterized by specifying that the second layer contains few or no fibers having diameter in the range of 2-10 μm, where few refers to less than 25%, or less than 20%, or less than 15%, or less than 10%, or less than 5%, or less than 1% of the fibers present in the second. Thus, the fibers become smaller with increasing distance from the base layer.

The optional third layer may be comprised of a plurality of particulate and/or fibrous elements that may exhibit enhanced lubricating and hydrating properties. The third layer may be comprised of bioabresorbable poly(ether)esters selected from homopolymers and copolymers, wherein the copolymers may exhibit segmented and/or block structures. Suitable bioabsorbable polyesters may be derived from at least one monomer selected from the group consisting of glycolide, L-lactide, DL-lactide, ε-caprolactone, trimethylene carbonate, para-dioxanone, and combinations thereof. The third layer may also include combinations with high molecular weight poly(ethers) such as poly(ethylene glycol), poly(ethylene oxide), biomolecules such as hyaluronic acid and its chemically modified derivatives, collagen, chondroitin sulfate, dermatan sulfate, bioactive peptides, glucosaminoglycan, oligosaccharides, and combinations thereof.

In one embodiment, the hydration gradient is formed by having an increasing content of poly(ethers), polyesters comprising etheric bond, and biomolecules with increasing content located distally away from the base layer in the z-axis (thickness). In some cases it may be preferable to have a hydration gradient in the x-y plane of the implantable device where localized regions exhibit a higher proportion hydrating elements. The hydration gradient is formed by the placement and dispensing of a hydrating element within the construct. By providing the increasing content of hydrating elements, the structure will be able to undergo rapid wetting afforded by the polarity of water, saline, and bodily fluids prior to implantation or use by the clinician. One benefit of this gradient is that it provides a physical appearance change when placed in the presence of a hydrating fluid and is able to provide a visual indication to the surgeon that the mesh has undergone wetting.

In one embodiment, a composite implant device may be provided. The implant device may display a laminate structure along with a gradient in hydration ability, lubricity, and mechanics.

In one embodiment, a composite implant can be structured and/or arranged to replace a tissue defect.

In one embodiment, the present disclosure provides a multi-layered implant device that is comprised of a base film layer, a fiber reinforced layer adjacent to the base layer, i.e., a first fibrous layer which is adjoined directly to the base layer, and additional superior fibrous layers, i.e., a second, third, fourth, etc. fibrous layer. Overall, the multi-layered construct is elastomeric. In addition, the multi-layered construct may feature one or more distinct surface morphologies and/or chemistries. In optional embodiments, the base film layer is defined by being (a) elastomeric; (b) thin; (c) has a low crystallinity; (d) can be dyed or tinted for visual detection, and/or (e) prevents the formation of tissue adhesions with the underlying viscera and/or organs. Mechanically, the base layer is the most elastic component of the implant and dominates the mechanical properties contributing greater than 50%, or 60%, or 70%, or 80%, or 90% of the tensile strength. The base layer also dominates the physical properties contributing more than 50% to the areal density and the thickness of the implant device. The base layer exhibits the lowest void volume (V1) of the various layers of the implant. The first fibrous layer is formed through an electrostatic deposition process where a polymer is deposited at a volumetric/mass flow rate of Q1. This layer is comprised of at least two polymers which are deposited separately wherein one polymer is elastomeric and the second polymer may or may not be elastomeric, where in one embodiment the second polymer is elastomeric and in another embodiment the second polymer is not elastomeric. The first fibrous layer has a higher void volume V2 compared to the void volume of the base layer V1, and also has a lower void volume compared to all other layers. The first fibrous layer requires some amount of the base film polymer in order to match the mechanics of the base layer close enough to resist delamination based on the mechanical mismatch of these layers. The first fibrous layer displays elastomeric properties, which are less than the elasticity of the base layer but higher than that of the additional superior fibrous layers. The additional superior fibrous layers are formed through an electrostatic deposition process where a polymer system is deposited at a volumetric/mass flow rate of Q2 wherein Q2<Q1 of the first fibrous layer. The superior fibrous layer displays the highest void volume fraction V3. The first fibrous layer and some layers of the superior fibrous layer can possess the same polymer composition wherein an elastomeric component is utilized, in various optional embodiments, at a ratio of 15%, or 20%, or 25%, or 30%, or 33%, or 35%, or 40% of fiber content. In one embodiment, the major component of these layers comprises a poly(ether ester) material.

In one embodiment, the present disclosure provides a multilayer construct, e.g., a mesh or laminate, where the construct comprises:
  a. a base layer comprising a synthetic polymer;
  b. a first fibrous layer adjoined directly to the base layer;
  c. a second fibrous layer adjoined directly to the first fibrous layer, wherein the first and second fibrous layers have non-identical properties.

For example, the first and second fibrous layers may have non-identical fiber populations, where the fibers of the first layer have a first average diameter and the fibers of the second layer have a second average diameter, where the two average diameters are non-identical, e.g., the first average diameter is greater than the second average diameter, e.g., the first layer has an average fiber diameter in the range of 2-10 μm while the second layer has an average fiber diameter in the range of 0.5-5 μm. Optionally, the first and second fibers are each prepared from synthetic polymer(s), so that synthetic polymer is present in each of the base layer, first fibrous layer and second fibrous layer.

Optionally, the multilayer construct may be further characterized by one or more of the embodiments disclosed herein, including one or more of the following numbered features, which include features specific to the base layer, and/or specific to the first layer, and/or specific to the second layer, and/or specific to both of the base and first layers, and/or specific to the second layer in relation to the base and/or first layers, and/or to an optional third layer which may be part of the construct, and/or to how two layers are combined or adjoined:

A. For example, in regard to the base layer, the construct may be further described by one or more of the embodiments:
  1) The construct wherein the base layer is bioresorbable, optionally completely bioresorbable, but optionally partially bioresorbable.
  2) The construct wherein the base layer is in the form of a sheet having a thickness of 25-500 microns, and the base layer does not contain pores.
  3) The construct wherein the base layer is in the form of a porous sheet, e.g., the base layer is in the form of a porous sheet having a thickness of 500-1000 microns, and/or the base layer has a porosity of less than 50%, which may be measured visually, e.g., Image J software available from National Institutes of Health, USA; and/or the base layer comprises a plurality of pores, and the plurality has an average pore diameter of less than 0.3 mm (300μ) or less than 0.5 mm (500 μm).
  4) The construct wherein the base layer has a first surface adjoining the first fibrous layer and a second surface which does not adjoin the first fibrous layer, the second surface having a texture other than a smooth texture, e.g., a roughened texture, where optionally the base layer comprises a material which induces a roughened texture, e.g., a material selected from the group consisting of polyether, salt, sugar, base, and organic biomolecule.
  5) The construct wherein the base layer has an areal density of 10-1000 $g/m^2$.
  6) The construct wherein the base layer has a strain-at-break of 100-2500%.
  7) The construct wherein the base layer comprises a colorant.
  B. For example, in regard to the first layer, the construct may be further described by one or more of the embodiments:
  8) The construct wherein the first layer comprises fibrous elements having a fiber diameter, wherein the fiber diameter is 0.001-1 mm.
  9) The construct wherein the first layer comprises electrospun fibers.
  10) The construct wherein the first layer comprises melt-extruded fibers.
  11) The construct wherein the first layer comprises wet spun fibers.
  12) The construct wherein the first layer comprises melt blown fibers.
  13) The construct wherein the first layer comprises knitted fibers.
  14) The construct wherein the first layer comprises braided fibers.
  15) The construct wherein the first layer comprises microfilaments, which refers to filaments having a diameter of less than 0.1 mm.

16) The construct wherein the first layer is a woven mesh, or alternatively the first layer is a knitted mesh.
17) The construct wherein the first layer is bioabsorbable, or alternatively, the first layer is non-absorbable.
18) The construct wherein the first layer comprises a first population of fibers and a second population of fibers, the fibers of the first population being different from the fibers of the second population.
19) The construct wherein the first layer comprises a first population of fibers and a second population of fibers, the fibers of the first population having a tensile strain at break of less than 100% and the second population having a tensile strain at break of greater than 100% with respect to the first population.
20) The construct wherein the first layer comprises a first population of fibers and a second population of fibers, the fibers of the first population having a tensile strain at break of less than 100% and the second population having a tensile strain at break of greater than 100% with respect to the first population, the first population of fibers comprising more fibers than the second population of fibers.
21) The construct wherein the first layer comprises a first population of fibers comprising collagen, and a second population of fibers, the first population being larger than the second population.
22) The construct wherein the first layer comprises a first population of fibers which are not elastomeric, and a second population of fibers which are elastomeric, the first population being greater than the second population.
23) The construct wherein the first layer comprises a first population of fibers comprising bioabsorbable polymer, and a second population of fibers comprising bioabsorbable fiber, wherein the bioabsorbable polymer of the first population of fibers is different from the bioabsorbable polymer of the second population of fibers.
C. For example, in regard to both of the base layer and the first layer, the construct may be further described by one or more of the embodiments:
24) The construct wherein the synthetic polymer in the base layer is also present in the first layer.
25) The construct wherein an elastomeric polymer is present in both the base layer and the first layer.
26) The construct wherein the base layer is elastomeric and the first layer is elastomeric.
27) The construct wherein delamination of the base layer from the first layer does not occur upon deformation of the construct.
28) The construct wherein a deforming load of 100% strain does not cause delamination of the base layer from the first layer.
29) The construct wherein a deforming load of 200% strain does not cause delamination of the base layer from the first layer.
30) The construct wherein a deforming load of 300% strain does not cause delamination of the base layer from the first layer.
31) The construct wherein a deforming load of 400% strain does not cause delamination of the base layer from the first layer.
32) The construct wherein a deforming load of 500% strain does not cause delamination of the base layer from the first layer.
33) The construct wherein a copolyester is present in both the base layer and the first layer.
34) The construct wherein both the base layer and the first layer are bioabsorbable.
35) The construct of embodiment 1 wherein the second layer comprises fibrous elements having a fiber diameter, wherein the fiber diameter is 0.001-1 mm.
D. For example, in regard to the second layer, the construct may be further described by one or more of the embodiments:
36) The construct wherein the second layer comprises electrospun fibers.
37) The construct wherein the second layer comprises melt-extruded fibers.
38) The construct wherein the second layer comprises melt blown fibers.
39) The construct wherein the second layer comprises knitted fibers.
40) The construct wherein the second layer comprises microfilaments.
41) The construct wherein the second layer is completely bioabsorbable, or alternatively, the second layer is partially bioabsorbable.
42) The construct wherein the second layer comprises a first population of fibers and a second population of fibers, the fibers of the first population being different from the fibers of the second population.
43) The construct wherein the second layer comprises a first population of fibers and a second population of fibers, the fibers of the first population having a tensile strain at break of less than 100% and the second population having a tensile strain at break of greater than 100% with respect to the first population.
44) The construct wherein the second layer comprises a first populations of fibers and a second population of fibers, the fibers of the first population in the second layer having a tensile strain at break of less than 100% and the second population in the second layer having a tensile strain at break of greater than 100% with respect to the first population, the first population of fibers in the second layer comprising more fibers than the second population of fibers in the second layer.
45) The construct wherein the second layer comprises a first populations of fibers comprising collagen, and a second population of fibers, the first population of the second layer being greater than the second population of the second layer.
46) The construct wherein the second layer comprises a first populations of fibers which are not elastomeric, and a second population of fibers which are elastomeric, the first population of the second layer being greater than the second population of the second layer.
47) The construct wherein the second layer comprises a first population of fibers comprising bioabsorbable polymer, and a second population of fibers comprising bioabsorbable fiber, wherein the bioabsorbable polymer of the first population of fibers in the second layer is different from the bioabsorbable polymer of the second population of fibers in the second layer.
E. For example, in regard to the second layer vis-à-vis one or both of the base layer and the first layer, the construct may be further described by one or more of the embodiments:
48) The construct wherein the synthetic polymer in the base layer is also present in the first layer and the second layer.
49) The construct wherein an elastomeric polymer is present in both the base layer, the first layer and the second layer.

50) The construct wherein a copolyester is present in the base layer, the first layer and the second layer.
51) The construct wherein each of the base layer, the first layer and the second layer are bioabsorbable.
52) The construct wherein the second layer may absorb more water than the first layer, and the first layer may absorb more water than the base layer.
53) The construct wherein the second layer has a greater lubricity than the first layer.
54) The construct wherein the second layer is an electrospun layer with a thickness, and the construct has a thickness, where the thickness of the electrospun layer is less than 50% of the thickness of the construct.

F. For example, in regard to an optional third layer, the construct may be further described by one or more of the embodiments:

55) The construct comprising a third layer, the third layer adjoining the second layer, the third layer comprising electrospun fiber.
56) The construct comprising a third layer, the third layer adjoining the second layer, the third layer having a thickness, and the construct having a thickness, where the thickness of the third layer is less than 50% of the thickness of the construct.
57) The construct wherein a third layer directly adjoins the second layer, and the third layer comprises fibrous elements.
58) The construct wherein a third layer directly adjoins the second layer, and the third layer is lubricious.
59) The construct wherein a third layer directly adjoins the second layer, and the third layer is hydrophilic.
60) The construct wherein a third layer directly adjoins the second layer, and the third layer comprises particulate elements.
61) The construct wherein a third layer directly adjoins the second layer, and the third layer comprises absorbable copolyester.
62) The construct wherein the third layer comprises polyethylene glycol.

G. For example, in regard to how the various layers are adjoined or combined, which may optionally characterize the construct, the construct may be further described by one or more of the embodiments:

63) The construct wherein the base layer is adjoined to the first layer by one of an adhesive, melting, solvent welding, ultrasonic welding, sewing, and physical entanglement.
64) The construct wherein the first layer is adjoined to the second layer by one of an adhesive, melting, solvent welding, ultrasonic welding, sewing, and physical entanglement
65) The construct wherein the base layer is adjoined to the first layer by a means which is also used to adjoin the first layer to the second layer.
66) The construct wherein the first layer is added to the base layer by an electrospinning technique.
67) The construct wherein the second layer is added to the first layer by an electrospinning technique.
68) The construct wherein the first layer is added to the base layer by an electrospinning technique utilizing a first mass addition rate, and the second layer is added to the first layer by an electrospinning technique utilizing a second mass addition rate, where the first mass addition rate is greater than the second mass addition rate.
69) The construct wherein a first polymer solution is applied to the base layer, and a second polymer solution is applied to the second layer, where the first polymer solution has a higher concentration of polymer than the second polymer solution.
70) The construct wherein the first layer is added to the base layer by an electrospinning technique utilizing a first mass addition rate, and the second layer is added to the first layer by an electrospinning technique utilizing a second mass addition rate, where the first mass addition rate is greater than the second mass addition rate.
71) The construct wherein a first polymer solution is applied to the base layer by an electrospinning technique utilizing a first mass addition rate, and a second polymer solution is applied to the second layer by an electrospinning technique utilizing a second mass addition rate, where the first polymer solution has a higher concentration of polymer than the second polymer solution, and the first and second mass addition rates are comparable.

The current technology is significantly different from related technologies based on two main premises: (1) the embodiments of the present disclosure do not need to be wholly or predominantly derived from biological tissue, and (2) embodiments of the present disclosure can replicate the structure and function of a biologically-derived mesh within a synthetic format where the majority of the construct is comprised of synthetic and bioabsorbable material.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

The following Examples are offered by way of illustration and not by way of limitation.

EXAMPLES

Example 1

An implant was prepared by dissolving an elastomeric, bioabsorbable polyaxial block copolymer, polymer 1, in chloroform overnight by continuous agitation to form a five (5) wt % solution. Following dissolution of the polymer, D&C Violet #2 was added at 40 ppm and agitated to form a homogenous tinted solution. The dissolved solution was volumetrically measured out and cast into an inert tray at a concentration of 0.5 mL/cm$^3$. The tray was covered with an inert, permeable cover to slow evaporation of the solvent.

After overnight (12 hr) evaporation, a solid elastomeric polymer film of 0.3-0.6 mm thickness, length of 100 mm, and width of 100 mm was obtained. The resultant film was fixed to a grounded stainless steel collector drum of diameter 12.7 cm and 25 cm in length. Two polymeric solutions were prepared by dissolution in hexafluoroisopropanol (HFIP). Solution 1 comprised of polymer 1 dissolved at a concentration of eight (8) wt %. Solution 2 comprised of linear poly(dioxanone) polymer dissolved at a concentration of nine (9) wt %.

The polymeric solutions were volumetrically dispensed out of two separate 20 gauge metallic spinnerets connected to a high voltage supply. Polymer solutions 1 and 2 were dispensed at ratio of 1:2, by controlling volumetric flow rate. Initial deposition rates for polymer solutions 1 and 2 were 5 ml/hr and 10 ml/hr, respectively, and both spinnerets were electrified with 21 kV and a working distance between the spinnerets and collector drum was 19 cm. The stainless steel collector drum was rotated at a linear velocity of 1 m/s. The first layer exhibited fiber diameters in the range of 2-10 µm. After one (1) hr deposition, the deposition rates were reduced to 2.5 ml/hr and 5 ml/hr for solutions 1 and 2, respectively.

The second layer exhibited fiber diameters in the range of 0.8-10 µm. After three (3) hours of deposition a third layer additional layer of electrostatic fibers was deposited by dispensing only polymer solution 2 at a volumetric flow rate of 2.5 ml/hr for an additional hour. The prepared implant device was removed from the collector drum and stored under vacuum (<1.5 Torr) until use.

Figure 5:
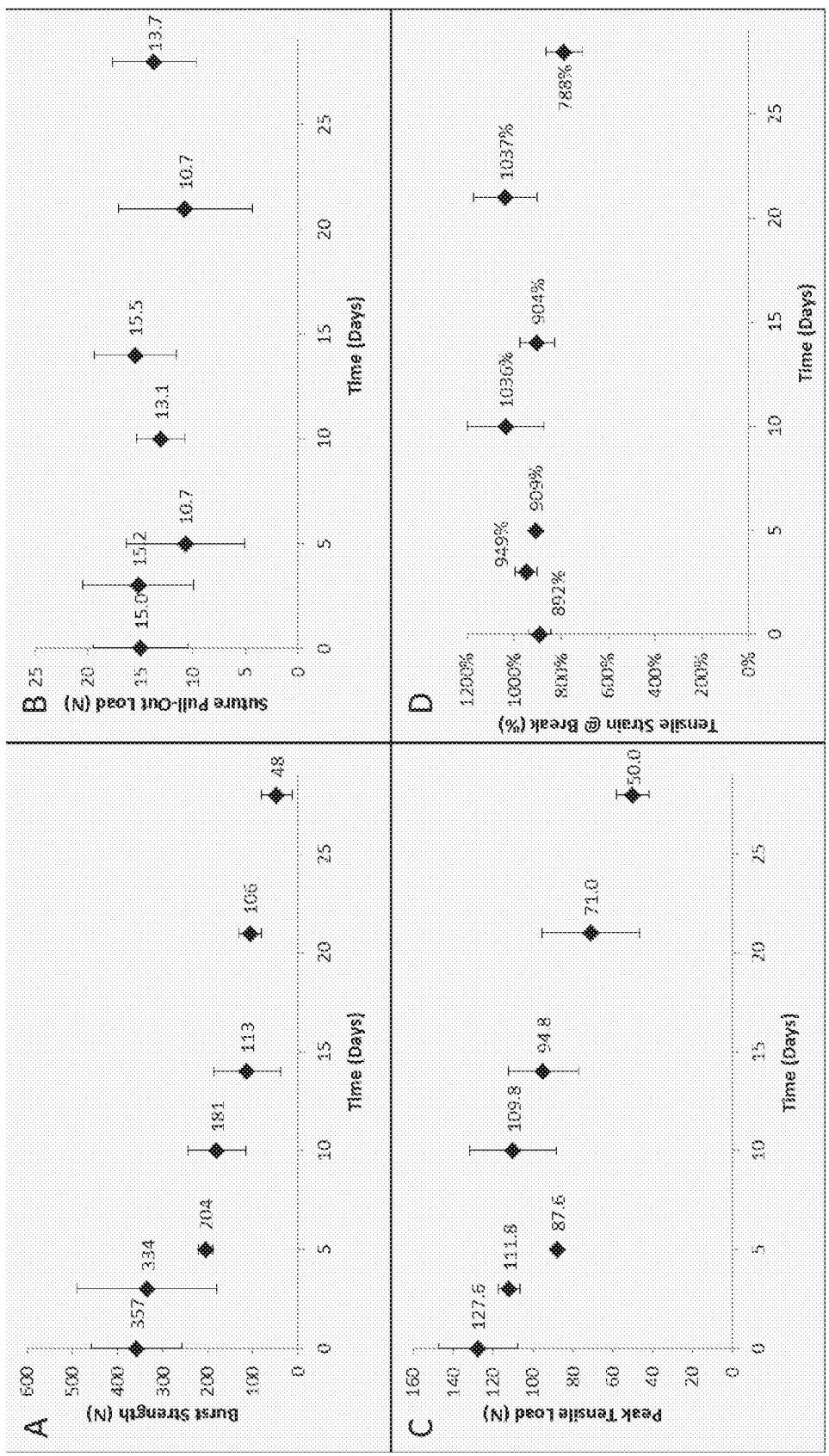
FIG. 5 shows data for constructs of the present disclosure as a function of degradation time, where panel (A) reports Burst Strength; panel (B) reports Suture Pull-Out Load; panel (C) reports Peak Tensile Load; and panel (D) reports Tensile Strain at Break.

The implant device from Example 1 was evaluated for physical and mechanical properties, as listed in Table 1 and as shown in FIG. 5. Thickness and areal density (mass per unit area) were determined by ASTM D177-96 and ASTM D 3776/3776M-09a, respectively. Tensile properties were determined by testing samples which were cut to 50 mm by 10 mm based on ASTM D 5034-09. Ball burst properties were determined by testing samples which were cut to 50 mm×50 mm based on ASTM D 3787-07. Suture pull-out properties were determined by testing samples which were cut to 25 mm by 25 mm, soaking samples in deionized water for 2 hours and threading a USP 3-0 polypropylene suture through the sample 7.5 mm from the edge of the cut sample at a testing rate of 50 mm/min. In vitro characterization of Example 1 was evaluated by incubating pre-cut samples in phosphate buffered saline (pH 7.4) maintained at 37° C. under orbital shaking of 75 rpm. In vitro properties evaluated included tensile mechanics (including tensile load, strength, elasticity), burst strength, and suture pull-out. Tensile mechanics indicated a decrease in both load and strength during a 28 day experiment with original tensile load of 127.6 N and a reduction to 50 N by day 28 (maintenance of ~40% strength). Burst mechanics also displayed a decrease in mechanics from 357 N at day 0 to 48 N at day 28. Tensile analysis did indicate a maintenance of stretch (strain at break) with initial values at 892% strain and day 28 values at 788% strain. Suture pull-out properties were also maintained throughout the in vitro examination with initial values at 15 N and final values at 13.7 N, indicated a maintenance of 91% of initial properties.

TABLE 1

| Property | Value |
| --- | --- |
| Thickness | 0.395 ± 0033 mm |
| Areal Density | 182 ± 76 g/m$^2$ |
| Tensile Modulus | 3.7 ± 0.7 MPa |
| Peak Tensile Load | 128 ± 20N |
| Tensile Elongation @ Break | 892 ± 46% |
| Ball Burst Strength | 356 ± 100N |
| Suture Pull-Out | 15 ± 4.5N |

Tissue integration and adhesion potential of Example 1 was assessed in a rabbit model (female, NZW, 3-3.5 kg) based on the approach used by Matthews et al. Journal of Surgical Research 123, 227-234 (2005). A bi-lateral approach was used where both sides of the underlying abdominal wall were used for mesh placement, thus maximizing the use of each animal and lowering the overall animal numbers while maintain a high level of statistical power. In this procedure Example 1 samples were placed on the right underside of the abdominal wall using an intraperitoneal implantation procedure. In this procedure, Example 1 was placed with the superior fibrous layer directly on an intact peritoneum and the base layer in direct contact with the viscera or subcutaneous tissue. Specifically, a 6 cm midline incision was made into the skin 2-3 cm below the xyphoid process. Next a 5 cm full thickness incision was created laterally along the midline. The incision was pulled back to allow placement of Example 1 materials on either side of the midline incision. A 3×3 cm mesh was placed in the left and right sides of the midline incision in direct contact with an intact peritoneum and secured with one knot of 5-O PDS II Monofilament Suture at each of the 4 corners of the mesh. The muscle at the incision site is closed over top using 4-O PDS II Monofilament Suture. The skin at the incision site was closed using 3-O PDS II Monofilament Suture followed by application of a small amount of tissue adhesive to seal the wound and reduce the risk of contamination. A total of six (6) animals were used. Mesh/tissue samples will be fixed in formalin and three (3) tissue cassettes will be created per mesh/tissue sample and sent for H&E staining by Histology Tech Services. All animals tolerated the surgeries and no complications were seen. After eight (8) weeks implantation animals were sacrificed by injection. Samples exhibited tissue ingrowth into the peritoneum with the superior fibrous layer and minimal adhesions associated with the underlying viscera that was in contact with the base layer.

Example 2

A composite implant device of the invention was prepared. The implant device displays an impregnated reinforced structure. The implant was prepared by the warp knitting of multifilament (filament count 10, denier 180 g/9000 m, tenacity of gf/denier) yarn comprising greater than 90% glycolide content into a Tricot pattern producing a porous mesh with a thickness of 0.3 mm, areal density of 75 g/m$^2$, and breaking strength N in both the machine and counter-machine direction. The mesh was coated with a polyaxial elastomeric bioabsorbable polyester polymer (polymer 1) coating. Polymer 1 was dissolved in chloroform overnight by continuous agitation to form a five (5) wt % solution. Following dissolution of the polymer, D&C Violet #2 was added at 40 ppm and agitated to form a homogenous tinted solution. The mesh was cut to 90 mm×90 mm in area and was centrally placed in an inert tray measuring 100 mm×100 mm×5 mm. The dissolved polymer solution was volumetrically measured out and cast into an inert tray at a concentration of 0.2-0.5 mL/cm$^2$. The tray was covered with an inert permeable cover to slow evaporation of the solvent. After overnight (12 hr) evaporation, a solid elastomeric reinforced polymer film of 0.4-0.5 mm thickness, length of 90 mm, and width of 90 mm was obtained. The resultant device comprised a base smooth film comprised of polymer 1, a reinforced film of mesh and polymer 1, and rough surface comprised of the mesh interrupting the film surface.

The prepared implant device was removed from the collector drum and stored under vacuum (<1.5 Torr) until use.

Figure 6:
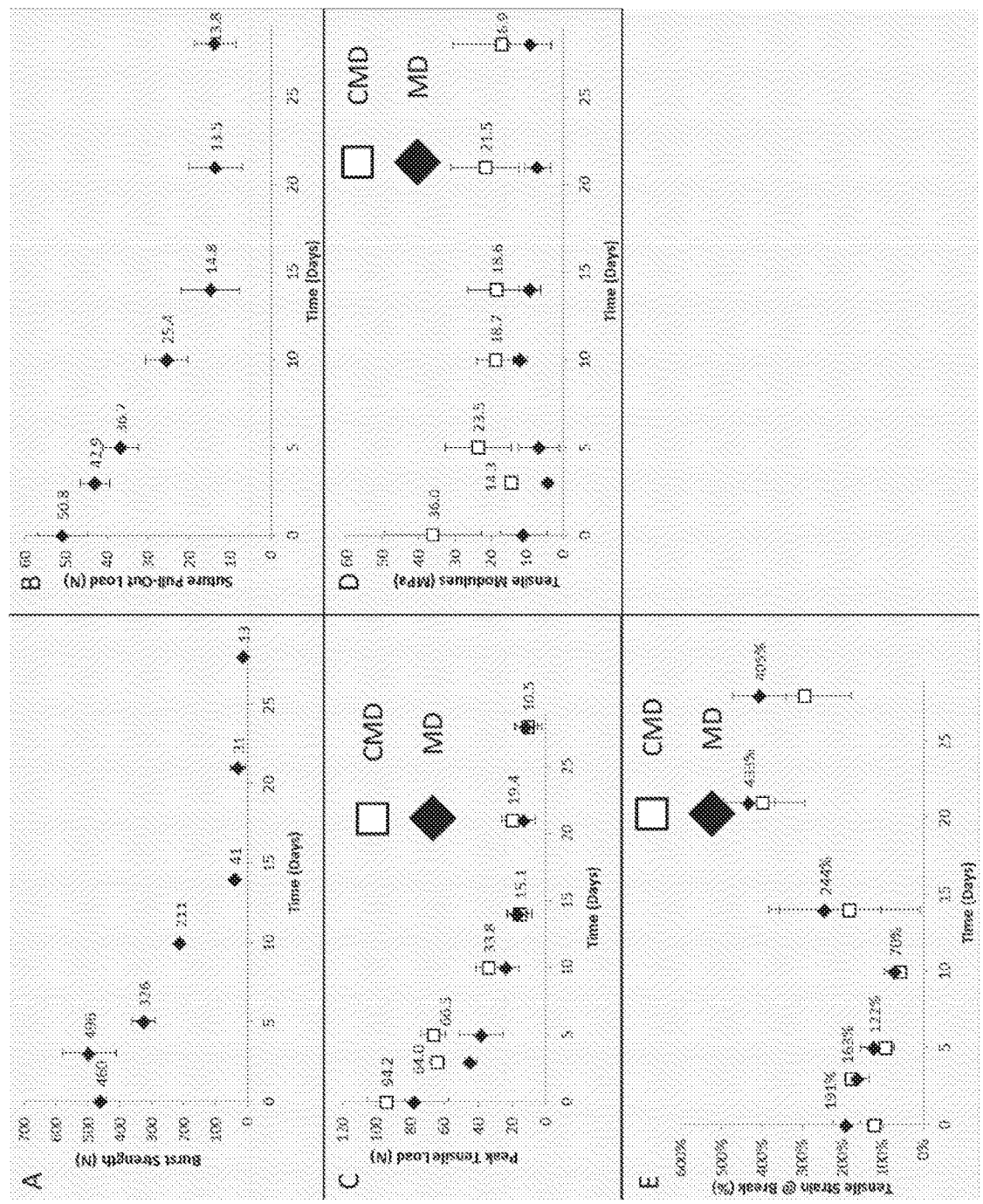
FIG. 6 shows data for constructs of the present disclosure as a function of degradation time, where panel (A) reports Burst Strength; panel (B) reports Suture Pull-Out Load; panel (C) reports Peak Tensile Load; panel (D) reports Tensile Modulus; and panel (E) reports Tensile Strain at Break.

The implant device from Example 2 was evaluated for physical and mechanical properties, as listed in Table 2 and as shown in FIG. 6, where MD=Machine Direction and CMD=Counter-machine direction. Thickness and areal density (mass per unit area) were determined by ASTM D177-96 and ASTM D 3776/3776M-09a, respectively. Tensile properties were determined by testing samples which were cut to 50 mm by 10 mm based on ASTM D 5034-09. Due to the anisotropic nature of the mesh used in Example 2, tensile properties were determined in both machine direction and counter-machine direction. Ball burst properties were determined by testing samples which were cut to 50 mm×50 mm based on ASTM D 3787-07. Suture pull-out properties were determined by testing samples which were cut to 25 mm by 25 mm, soaking samples in deionized water for 2 hours and threading a USP 3-0 polypropylene suture through the sample 7.5 mm from the edge of the cut sample at a testing rate of 50 mm/min. Suture pull-out properties were determined in the counter-machine direction. In vitro characterization of Example 2 was evaluated by incubating pre-cut samples in phosphate buffered saline (pH 7.4) maintained at 37° C. under orbital shaking of 75 rpm. In vitro properties evaluated included tensile mechanics (including tensile load, strength, elasticity), burst strength, and suture pull-out. Tensile mechanics indicated a decrease in both machine and counter machine directions for both load and strength during a 28 day experiment with original tensile loads at 100 N and 80 N and reductions to 15 N by day 28 (maintenance of ~15% strength). Burst mechanics also displayed a significant decrease in mechanics from 460 N at day 0 to 13 N at day 28. Tensile analysis did indicate an increase in stretch (strain at break) with initial values below 200% strain and day 28 values greater than 400% strain. This change in strain be attributed to degradation of the fiber reinforced component allowing the properties of the base component to become un-restrained allowing extension of the construct. Suture pull-out properties decreased throughout the in vitro examination with initial values at 45 N and final values at 15 N, indicated a maintenance of 30% of initial properties.

TABLE 2

| Property | Value |
| --- | --- |
| Thickness | 0.3888 ± 0.055 mm |
| Areal Density | 233 ± 92 g/m² |
| Tensile Modulus | MD: 10.9 ± 6.6 MPa |
|  | CMD: 36 ± 13.3 MPa |
| Peak Tensile Load | MD: 77.6 ± 20.1N |
|  | CMD: 94.2 ± 10.9N |
| Tensile Elongation @ Break | MD: 191 ± 34% |
|  | CMD: 121 ± 19% |
| Ball Burst Strength | 459 ± 17N |
| Suture Pull-Out | 51 ± 6.1N |

Example 3

A composite implant device of the invention was prepared according to the following procedure. The implantable device of Example 2 was produced and further modified to incorporate fibrous elements on the roughened side of the implant device. The resulting implant device was fixed (secured) to a grounded stainless steel collector drum of diameter 12.7 cm and 25 cm in length. Two polymeric solutions were prepared. Solution 1 was made by dissolving polyethylene oxide (molecular weight of 20,000 Da) in deionized water at a concentration of six (6) wt %. Solution 2 was made by dissolving a poly(ether-ester) block copolymer in hexafluorisopropanol (HFIP) at a concentration of eight (8) wt %). The poly(ether-ester) was a triblock copolymer comprised of a central hydrophilic block derived from poly(ethylene glycol) (molecular weight of 12,000 Da) and flanking poly(ether-ester) blocks derived from para-dioxanone.

The polymeric solutions were volumetrically dispensed out of two separate 20 gauge metallic spinnerets connected to a high voltage supply. Polymer solutions 1 and 2 were dispensed at an equal ratio of 1:1, by controlling volumetric flow rate with the collector drum rotating at a linear velocity of 2 m/s. Initial deposition rates for polymer solutions 1 and 2 were 5 ml/hr, and both spinnerets were electrified with 25 kV and a working distance between the spinnerets and collector drum was 19 cm. The first fibrous layer exhibited fiber diameters in the range of 1-10 After three (3) hours of deposition an additional layer of electrostatic fibers was deposited by dispensing only polymer solution 1 at a volumetric flow rate of 2.5 ml/hr for an additional hour. The prepared implant device was removed from the collector drum and stored under vacuum (<1.5 Torr) until use.

Example 4

Figure 7:
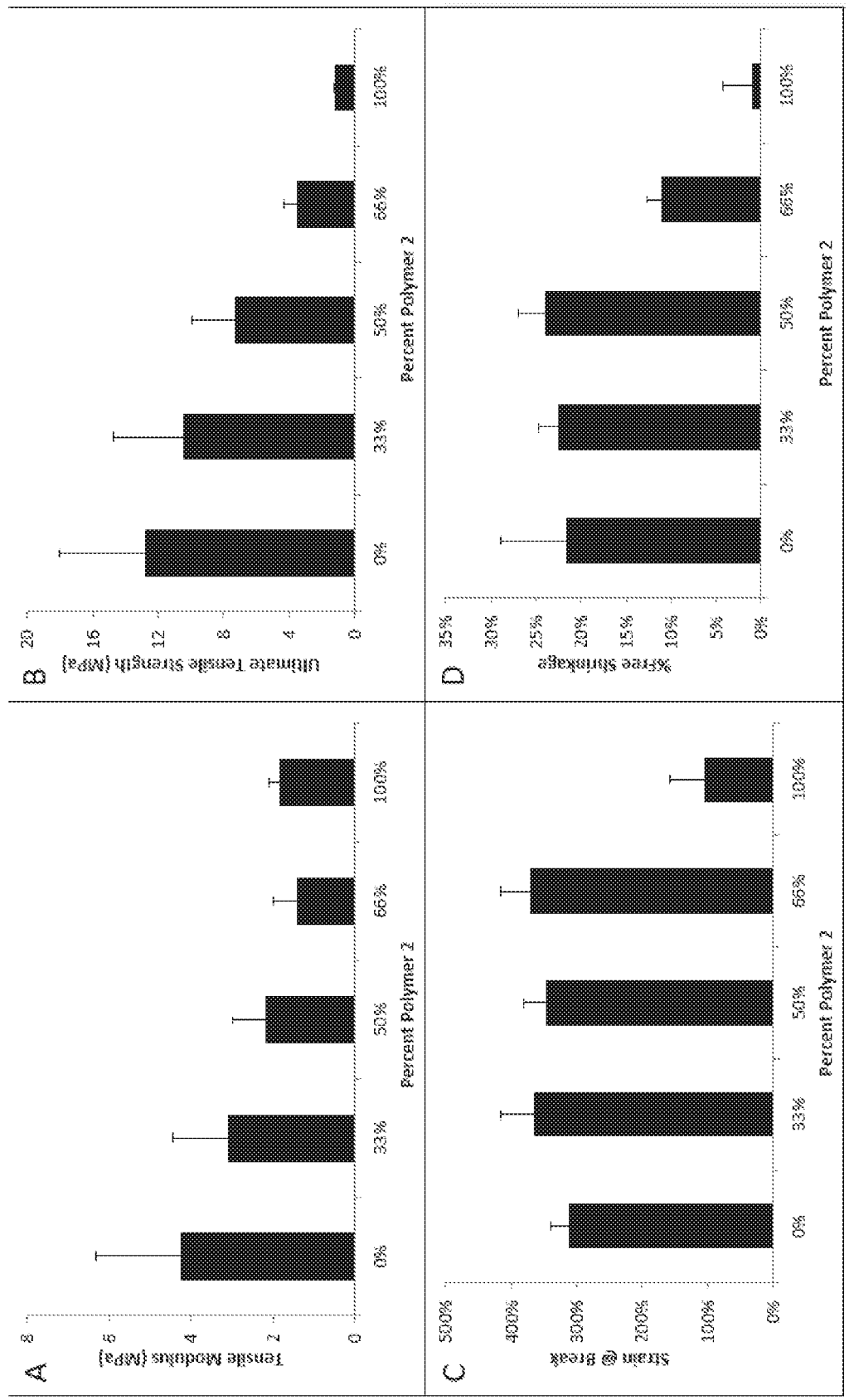
FIG. 7 shows data for constructs of the present disclosure as a function of polymer 2 content, where panel (A) reports Tensile Modulus; panel (B) reports Ultimate Tensile Strength; panel (C) reports Strain at Break; and panel (D) reports % Free Shrinkage.

Fiber laminates were produced by electrospinning of two (2) separate polymer solutions at varying flow rates and ratios to determine effects of inclusion of each fiber population within the final construct. Polymer solution 1 and 2 were dispensed at varying flow rates to demonstrate effect of incorporating non-elastomeric materials into the first and second layer of the invention. Introduction of the non-elastic material significantly decreased both tensile modulus and tensile strength. Introduction of polymer solution 2, significantly reduced these properties at values starting at 33% by mass, see FIG. 7, panels (A), (B), (C) and (D). For example, as shown in FIG. 7 panel (C), strain at break for the fiber laminates was maintained with fiber populations up to 66%. In addition to maintaining strain at break, free shrinkage for the major elastomeric component significantly decreased at 66% loading content.

Example 5

An implant was prepared by dissolving an elastomeric, bioabsorbable polyaxial block copolymer, polymer 1, in chloroform overnight by continuous agitation to form a five (5) wt % solution. Following dissolution of the polymer, D&C Violet #2 was added at 40 ppm and agitated to form a homogenous tinted solution. The tinted solution was volumetrically measured out and cast into an inert tray at a concentration of 0.5 mL solution/cm² tray surface. The tray was covered with an inert, permeable cover to slow evaporation of the solvent.

After overnight (12 hr) evaporation, a solid elastomeric polymer film of 0.3-0.6 mm thickness, length of 100 mm, and width of 100 mm was obtained. The resultant film provided a base layer for a multilayer construct of the present disclosure.

The resultant film was fixed to a grounded stainless steel collector drum of diameter 12.7 cm and 25 cm in length. Two polymeric solutions were prepared by dissolution in hexafluoroisopropanol (HFIP). Solution 1 comprised polymer 1 dissolved at a concentration of eight (8) wt %.

Solution 2 comprised linear poly(dioxanone) polymer dissolved at a concentration of nine (9) wt %.

The polymeric solutions were volumetrically dispensed out of two separate 20 gauge metallic spinnerets connected to a high voltage supply. Polymer solutions 1 and 2 were dispensed at ratio of 1:2, by controlling volumetric flow rate. Deposition rates were varied for polymer solutions 1 and 2 and both spinnerets were electrified with 21 kV and a working distance between the spinnerets and collector drum was 19 cm. The stainless steel collector drum was rotated at a linear velocity of 1 m/s.

This process provided both a first fibrous layer and a second fibrous layer. The first layer exhibited fiber diameters in the range of 2-10 µm. The second layer exhibited fiber diameters in the range of 0.5-5 µm.

Figure 8:
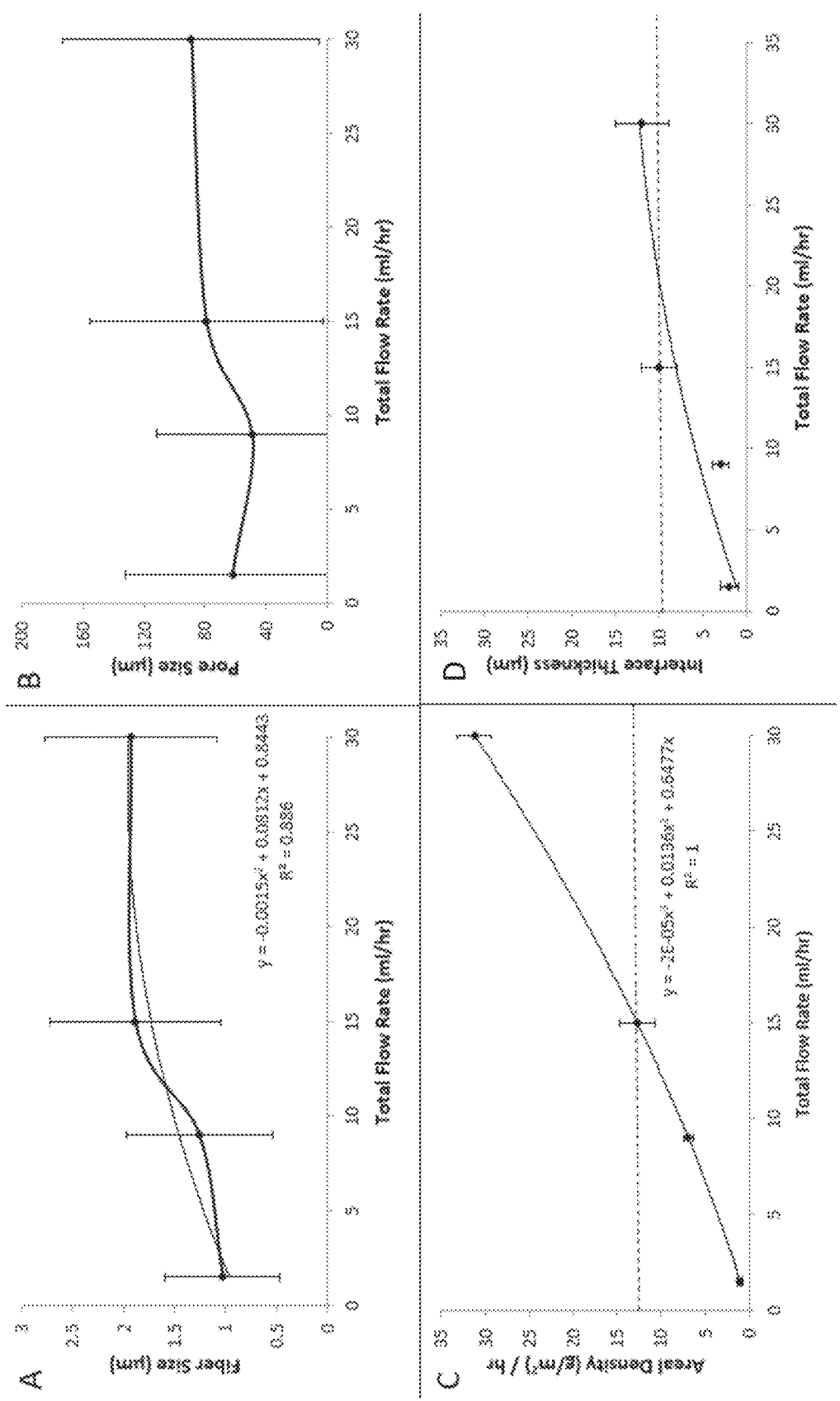
FIG. 8 shows data for constructs of the present disclosure as a function of total flow rate, where panel (A) reports fiber size, panel (B) reports pore size, panel (C) reports areal density, and panel (D) reports interface thickness.
Figure 9:
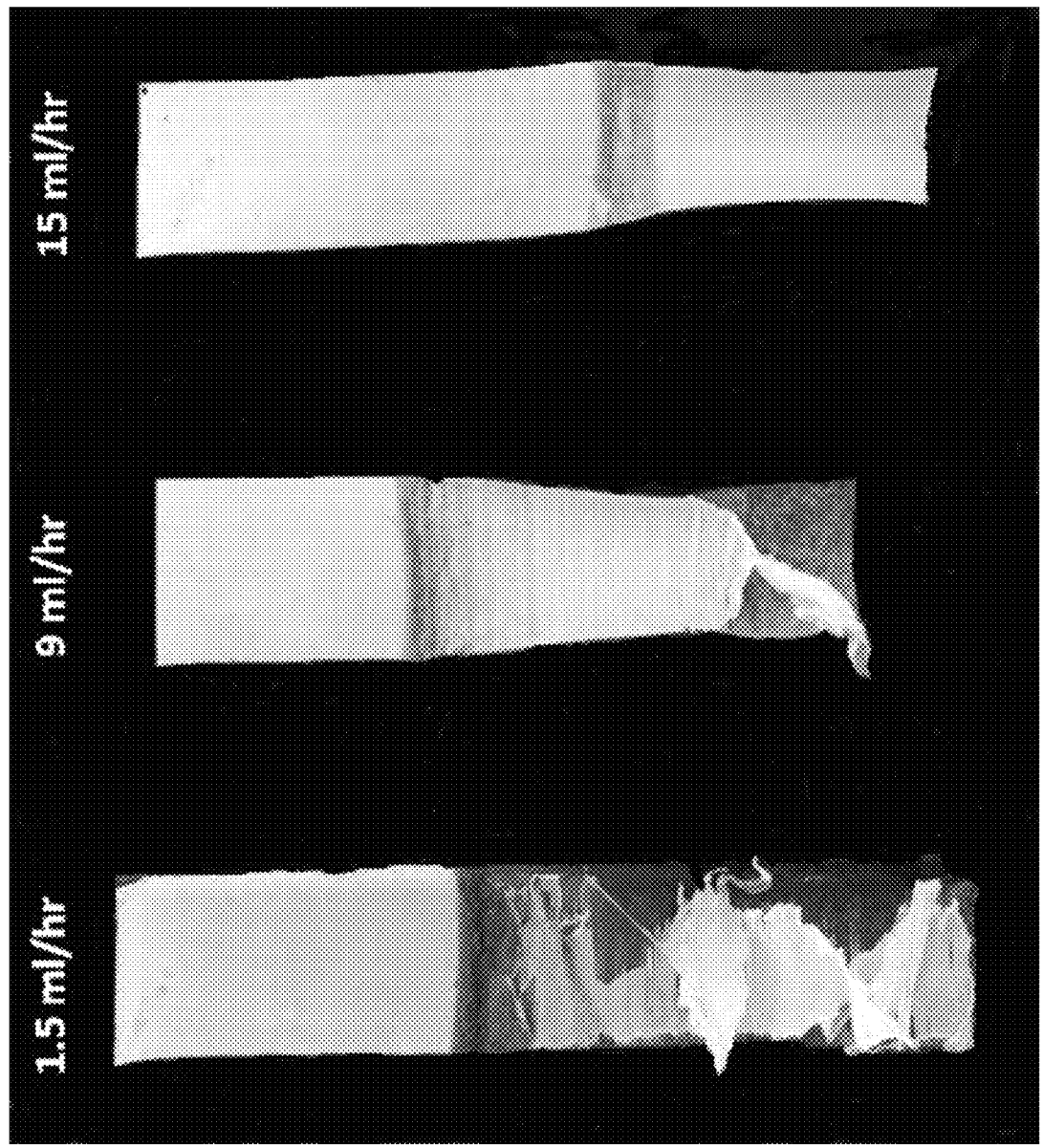
FIG. 9 are images that show the effect of load on delamination for constructs of the present disclosure, where constructs prepared at faster polymer deposition rate, e.g., 15 mL/hr generally exhibit less delamination than construct prepared at a slower rate, e.g., 1.5 mL/hr.

After one (1) hr deposition samples were assessed by electron microscopy, with results shown in FIG. 8, where panel (A) describes fiber size, panel (b) describes pore size, panel (C) describes areal density, and panel (D) describes interface thickness, each as a function of total flow rate. Thus, panel (A) of FIG. 8 shows that fiber size increased with total flow rate of polymer solutions 1 and 2 with a correlation factor of 0.88. Combinatorial volumetric flow rates did not lead to a strong correlation with pore size though a weak positive correlation was observed. Areal density for the fiber reinforced layer indicated that at a combinatorial flow rate of 15 ml/hr yielded an areal density deposition rate of 12 g/m$^2$-hr.

At a combinatorial flow rate of 15 ml/hr it was observed to have morphological changes to the base layer surface indicated a fiber reinforced morphology or partial loss of fibrous features. Partial loss of fibrous features allowed integration of the polymer solutions into the resultant film surface which provided a first fibrous layer which was directly adjoined to the base layer. The formation of this first layer is facilitated when the polymer(s) that form the base layer have solubility in the solvent(s) used to deliver polymer 1 and/or polymer 2. The second fibrous layer was directly adjoined to the first fibrous layer, but did not contact the baser layer.

Example 6

A composite implant device of the present disclosure was prepared, which includes an impregnated reinforced structure as the first fibrous layer. The implant was prepared by the weft knitting of monofilament (0.08 mm diameter, tenacity of ≥3 gf/denier) fiber comprising greater than 90% glycolide content doubled with a Type I Collagen fiber into a Tricot pattern producing a porous mesh with a thickness of 0.3 mm, areal density of 60-70 g/m$^2$, and breaking strength ≥40 N in the machine direction. The Type I Collagen fiber was produced using techniques known in the field as reported by Caves J M et al., see, e.g., Biomaterials. 2011 August; 32(23):5371-9 and J Biomed Mater. Res. B Appl. Biomater. 2010 April; 93(1):24-38. The mesh was coated with a polyaxial elastomeric bioabsorbable polyester polymer (polymer 1) coating. Polymer 1 was dissolved in chloroform overnight by continuous agitation to form a five (5) wt % solution. Following dissolution of the polymer, D&C Violet #2 was added at 40 ppm and agitated to form a homogenous tinted solution. The mesh was cut to 90 mm×90 mm in area and was centrally placed in an inert tray measuring 100 mm×100 mm×5 mm. The dissolved polymer solution was volumetrically measured out and cast into an inert tray at a concentration of 0.2-0.5 mL/cm$^2$. The tray was covered with an inert permeable cover to slow evaporation of the solvent. After overnight (12 hr) evaporation, a solid elastomeric reinforced polymer film of 0.4-0.5 mm thickness, length of 90 mm, and width of 90 mm was obtained. The resultant device comprised a base layer in the form of a nonporous smooth film comprised of polymer 1, a first fibrous layer in the form of a reinforced film of mesh and polymer 1, and a second fibrous layer in the form of a rough surface on top of the first fibrous layer which comprised of the impregnated mesh interrupting the film surface of the first fibrous layer. The prepared implant device was removed from the collector drum and stored under vacuum (<1.5 Torr) until use.

Example 7

Implants were prepared by dissolving an elastomeric, bioabsorbable polyaxial block copolymer, polymer 1, in chloroform overnight by continuous agitation to form a five (5) wt % solution. Following dissolution of the polymer, D&C Violet #2 was added at 40 ppm and agitated to form a homogenous tinted solution. The dissolved solution was volumetrically measured out and cast into an inert tray at a concentration of 0.5 mL/cm$^2$. The tray was covered with an inert, permeable cover to slow evaporation of the solvent.

After overnight (12 hr) evaporation, a solid elastomeric polymer films of 0.3-0.6 mm thickness, length of 100 mm, and width of 100 mm was obtained. The resultant film was fixed to a grounded stainless steel collector drum of diameter 12.7 cm and 25 cm in length. Two polymeric solutions were prepared by dissolution in hexafluoroisopropanol (HFIP). Solution 1 comprised of polymer 1 dissolved at a concentration of eight (8) wt %. Solution 2 comprised of linear poly(dioxanone) polymer dissolved at a concentration of nine (9) wt %.

The polymeric solutions were volumetrically dispensed out of two separate 20 gauge metallic spinnerets connected to a high voltage supply. Polymer solutions 1 and 2 were dispensed at ratio of 1:2, at varying volumetric flow rates. Three (3) samples were produced where polymer solutions 1 and 2 were dispensed at the following rates: 0.5 ml/hr and 1 ml/hr, 3 ml/hr and 6 ml/hr, and 5 ml/hr and 10 ml/hr, respectively and are summarized in the table below.

TABLE 3

| Trial | Polymer 1 Flow Rate | Polymer 2 Flow Rate | Total Flow Rate |
|---|---|---|---|
| 1 | 0.5 ml/hr | 1 ml/hr | 1.5 ml/hr |
| 2 | 3 ml/hr | 6 ml/hr | 9 ml/hr |
| 3 | 5 ml/hr | 10 ml/hr | 15 ml/hr |

In all trials, spinnerets were electrified with 21 kV and a working distance between the spinnerets and collector drum was 19 cm. The stainless steel collector drum was rotated at a linear velocity of 1 m/s. The first layer exhibited fiber diameters in the range of 2-10 µm. After one (1) hr deposition, the deposition rates were changed to 2.5 ml/hr and 5 ml/hr for solutions 1 and 2, respectively.

After three (3) hours of deposition a third layer additional layer of electrostatic fibers was deposited by dispensing only polymer solution 2 at a volumetric flow rate of 2.5 ml/hr for an additional hour. The prepared implant device was removed from the collector drum and stored under vacuum (<1.5 Torr) until use. Samples from the trials were evaluated for tensile properties and more importantly for delamination of the fibrous layer from the base layer. As presented in FIG.

9, total flow rates at 9 ml/hr or less resulted in constructs where delamination (separation of the fibrous layer with the base layer) occurred.

Thus, in one embodiment the present disclosure provides a multilayer construct wherein a fibrous material in the form of a porous mesh is partially encased within a layer of polymer to provide a first fibrous layer (the first fibrous layer being the layer that comprises (a) porous mesh fully encased within a layer of the polymer, and (b) the polymer in the form of a film that fully encases the porous mesh), and where that polymer extends on one side of the first layer to provide a mesh-free base layer that comprises the polymer but not a fibrous component, and the porous mesh extends from the opposite side of the first layer without being fully encased within a layer of polymer that is present in the first fibrous layer, to provide a second fibrous layer (where the second fibrous layer is not fully encased by a layer or film the polymer), where the fibrous material of the second fibrous layer may optionally be coated with the polymer of the first fibrous layer, but not fully encased by a layer of the polymer of the first fibrous layer.

In addition, the present disclosure provides a method of making a multilayer construct comprising (a) forming a porous mesh from a polymeric filament; (b) submerging the porous mesh in a solution comprising a film-forming polymer and a volatile solvent; (c) allowing the porous mesh to float on the solution so that some of the porous mesh extends above the surface of the solution and none of the porous mesh extends to the bottom of the solution; and (d) evaporating the solvent to provide a multilayer construct of the present disclosure. The method may be used to prepare a multilayer construct wherein a fibrous material in the form of a porous mesh is partially encased within a layer of polymer to provide a first fibrous layer (the first fibrous layer being the layer that comprises (a) porous mesh fully encased within a layer of the polymer, and (b) the polymer in the form of a film that fully encases the porous mesh), and where that polymer extends on one side of the first layer to provide a mesh-free base layer that comprises the polymer but not a fibrous component, and the porous mesh extends from the opposite side of the first layer without being fully encased within a layer of polymer that is present in the first fibrous layer, to provide a second fibrous layer (where the second fibrous layer is not fully encased by a layer or film the polymer), where the fibrous material of the second fibrous layer may optionally be coated with the polymer of the first fibrous layer, but not fully encased by a layer of the polymer of the first fibrous layer.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless specifically stated, terms and phrases used in this document, and variations thereof, unless otherwise expressly stated, should be construed as open ended as opposed to limiting.

Furthermore, although items, elements or components of the disclosure may be described or claimed in the singular, the plural is contemplated to be within the scope thereof unless limitation to the singular is explicitly stated. Thus, it is to be understood that as used herein and in the appended claims, the singular forms "a," "an," and "the" include plural reference unless the context clearly dictates otherwise.

The presence of broadening words and phrases such as "one or more," "at least," "but not limited to" or other like phrases in some instances shall not be read to mean that the narrower case is intended or required in instances where such broadening phrases may be absent.

It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas, so that the term "X and/or Y" means "X" or "Y" or both "X" and "Y". A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

The letter "s" following a noun designates both the plural and singular forms of that noun, where the designation "(s)" may alternatively be used to provide the same meaning.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed the text are provided solely for their disclosure prior to the filing date of the present application. Nothing herein is to be construed as an admission that the inventors are not entitled to antedate any referenced publication by virtue of prior invention. All patents, publications, scientific articles, web sites, and other documents and materials referenced or mentioned herein are indicative of the levels of skill of those skilled in the art to which the invention pertains. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicant.

What is claimed is:

1. A method for forming a multilayer construct, the method comprising:
    a) providing an elastomeric base layer comprising a first synthetic polymer;
    b) using an electrospinning technique to apply a first solution comprising the first synthetic polymer to the base layer, to provide a first fibrous layer which is elastomeric and directly adjoins the base layer;
    c) using an electrospinning technique to apply a second solution comprising a second synthetic polymer to the first fibrous layer, to provide a second fibrous layer which directly adjoins the first fibrous layer;
    wherein the first and second fibrous layers have non-identical properties in terms of average diameter of the fibers contained therein such that the fibers of the first fibrous layer have an average diameter which is greater than an average diameter of the fibers of the second fibrous layer.

2. The method of claim 1 wherein the base layer is prepared by solvent casting a solution comprising the first synthetic polymer to provide a solid elastomeric film as the base layer.

3. The method of claim 1 wherein the base layer is in the form of a non-porous, elastomeric sheet.

4. The method of claim 1 wherein in step a), the base layer is affixed to a grounded stainless steel drum.

5. The method of claim 1 wherein the base layer and the first solution each comprises a copolyester.

6. The method of claim 1 wherein each of the base layer, the first layer and the second layer are bioabsorbable.

7. The method of claim 1 wherein the first solution and the second solution each comprises hexafluoroisopropanol.

8. The method of claim 1 wherein the base layer has a strain-at-break of 100-2500%.

9. The method of claim 1 wherein the second layer comprises fibers, each fiber having a fiber diameter, wherein the fiber diameter is 0.001-1 mm.

* * * * *